(12) United States Patent
Abbott et al.

(10) Patent No.: US 7,724,319 B2
(45) Date of Patent: May 25, 2010

(54) DETECTING INTERACTIONS AT BIOMIMETIC INTERFACES WITH LIQUID CRYSTALS

(75) Inventors: Nicholas L. Abbott, Madison, WI (US); Jeffrey M. Brake, Newark, DE (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/324,403

(22) Filed: Nov. 26, 2008

(65) Prior Publication Data

US 2009/0123670 A1 May 14, 2009

Related U.S. Application Data

(62) Division of application No. 11/523,319, filed on Sep. 19, 2006, now Pat. No. 7,459,124, which is a division of application No. 10/119,648, filed on Apr. 10, 2002, now Pat. No. 7,125,592.

(51) Int. Cl.
| | |
|---|---|
| G02F 1/13 | (2006.01) |
| G02F 1/1333 | (2006.01) |
| G01N 33/53 | (2006.01) |
| G01N 33/566 | (2006.01) |
| G01N 21/21 | (2006.01) |
| G01N 21/75 | (2006.01) |
| G01N 21/85 | (2006.01) |

(52) U.S. Cl. ............................ 349/58; 349/199; 436/4; 436/501; 436/805; 422/55

(58) Field of Classification Search ................. 349/58, 349/199; 436/4, 501, 805; 422/55
See application file for complete search history.

(56) References Cited

U.S. PATENT DOCUMENTS 4,597,942 A    7/1986    Meathrel (Continued)

FOREIGN PATENT DOCUMENTS

DE          3617710 A1    12/1986

(Continued)

OTHER PUBLICATIONS

Ennulat, R. D. et al., "Thermal Radiography Utilizing Liquid Crystals," Molecular Crystals and Liquid Crystals, vol. 13, pp. 149-164, 1971; published by Gordon and Breach Science Publishers (United Kingdom).

(Continued)

*Primary Examiner*—Shean C Wu
(74) *Attorney, Agent, or Firm*—Quarles & Brady LLP

(57) ABSTRACT

A method of forming a liquid crystal device, includes: contacting an aqueous solution comprising a surfactant and a receptor molecule with a top surface of a liquid crystal. The liquid crystal is in a holding compartment of a substrate, and the receptor molecule is adsorbed on the top surface of the liquid crystal forming an interface between the liquid crystal and the aqueous solution. The receptor molecule is different than the surfactant. A method of detecting a compound in a flowing stream includes passing an aqueous solution over a top surface of a liquid crystal in a holding compartment of a substrate. The method also includes determining whether a change in the orientation of the liquid crystal occurs as the aqueous solution is passed over the top surface of the liquid crystal. A change in the orientation of the liquid crystal indicates the presence of the compound in the flowing stream.

5 Claims, 13 Drawing Sheets

U.S. PATENT DOCUMENTS

| | | | |
|---|---|---|---|
| 4,628,037 | A | 12/1986 | Chagnon et al. |
| 4,725,669 | A | 2/1988 | Essex et al. |
| 4,812,556 | A | 3/1989 | Vahlne et al. |
| 5,620,850 | A | 4/1997 | Bamdad et al. |
| 5,712,103 | A | 1/1998 | Leavitt et al. |
| 6,060,327 | A | 5/2000 | Keen |
| 6,159,681 | A | 12/2000 | Zebala |
| 6,171,802 | B1 | 1/2001 | Woolverton et al. |
| 6,277,489 | B1 | 8/2001 | Abbott et al. |
| 6,284,197 | B1 | 9/2001 | Abbott et al. |
| 6,288,392 | B1 | 9/2001 | Abbott et al. |
| 6,306,594 | B1 | 10/2001 | Cozzette et al. |
| 7,125,592 | B2 * | 10/2006 | Abbott et al. ................ 428/1.5 |
| 7,459,124 | B2 * | 12/2008 | Abbott et al. ................ 422/55 |

FOREIGN PATENT DOCUMENTS

| | | |
|---|---|---|
| EP | A284587 | 8/1988 |
| EP | 0345462 | 12/1989 |
| JP | 02311822 A2 | 12/1990 |
| JP | 02311824 A2 | 12/1990 |
| JP | 03010222 A2 | 1/1991 |
| JP | 03039932 A2 | 2/1991 |
| JP | 04057024 A2 | 2/1992 |
| JP | 04057025 A2 | 2/1992 |
| JP | 04284423 A2 | 10/1992 |
| JP | 05134257 A2 | 5/1993 |
| JP | 05134258 A2 | 5/1993 |
| JP | 06175136 A2 | 6/1994 |
| JP | 06194513 A2 | 7/1994 |
| JP | 06194662 A2 | 7/1994 |
| WO | 92/08978 | 5/1992 |
| WO | 99/63329 | 12/1999 |
| WO | 99/64862 | 12/1999 |
| WO | 01/61325 | 8/2001 |
| WO | 01/61357 | 8/2001 |

OTHER PUBLICATIONS

Novak, T.J. et al., "Use of Anisotropic Materials as Chemical Detectors," Analytical Letters, vol. 5, No. 3, pp. 187-192, 1972, published by Marcel Dekker, Inc. (New York, NY).

Poziomek, E.J. et al., "Use of Liquid Crystals as Vapor Detectors," Mol. Cryst. Liq. Cryst., vol. 27, pp. 175-185, 1973, published by Gordon and Breach Science Publishers, Ltd., (Holland).

Saji, T. et al., "Reversible Formation and Disruption of Micelles by Control of the Redox State of the Head Group," J. Am. Soc., vol. 107, pp. 6865-6868, 1985, published by the American Chemical Society (Washington, D.C.).

Heslot, F. et al., "Molecular Layering in the Spreading of Wetting Liquid Drops," Nature, vol. 338, pp. 640-642, 1989, published by Nature Publishing (New York, NY).

Pieranski P. et al., "Adsorption-Induced Anchoring Transitions at Nematic-Liquid-Crystal-Crystal Interfaces," Phys. Rev. A., vol. 40, No. 1, pp. 317-322, Jul. 1, 1989, published by the American Physical Society (Washington, D.C.).

Starkey, C.A. et al., "Evaluation of the Recombigen HIV-1 Latex Agglutination Test," J. Clin. Microbiol., vol. 28, No. 4, pp. 819-822, Apr. 1990, published by the American Society for Microbiology (Washington, D.C.).

Parish et al., "A Polyanion Binding Site on the CD4 Molecule, Proximity to the HIV-gp120 Binding Region," The Journal of Immunology, vol. 145, No. 4, pp. 1188-1195, Aug. 15, 1990, published by the American Association of Immunologists, Inc. (Bethseda, MD).

Häussling, L. et al., "Biotin-Functionalized Self-Assembled Monolayers on Gold: Surface Plasmon Optical Studies of Specific Recognition Reactions," Langmuir, vol. 7, No. 9, pp. 1837-1840, Sep. 1991, published by the American Chemical Society (Washington, D.C.).

Jérôme, B., "Surface Effects and Anchoring in Liquid Crystals," Rep. Prog. Phys. vol. 54, pp. 391-452, 1991, published by IOP publishing Ltd. (United Kingdom).

Saji, T. et al., "Formation of Organic Thin Films by Electrolysis of Surfactants with the Ferrocenyl Moiety," J. Am. Chem. Soc., vol. 113, pp. 450-456, 1991, published by the American Chemical Society (Washington, D.C.).

Schmitt, F.-J. et al., "Surface Plasmon Studies of Specific Recognition Reactions at Self-Assembled Monolayers on Gold," Thin Solid Films, vol. 210/211, pp. 815-817, 1992, published by Elsevier Sequoia.

Charych, D.H. et al., "Direct Colorimetric Detection of a Receptor-Ligand Interaction by a Polymerized Bilayer Assembly", Science, vol. 261, pp. 585-588, Jul. 30, 1993, published by the American Association for the Advancement of Science (Washington, D.C.).

Cocchi, J.M. et al., "Comparison Between Direct Binding, Competition and Agglutination Assays in the Characterization of Polyclonal Anti-idiotypes Against Anti-HBs Human Monoclonal Antibodies," Immunological Meth., vol. 160, pp. 1-9, 1993, Elsevier Science Publishers.

H. Weetall. "Preparation of Immobilized Proteins Covalently Coupled Through Silane Coupling Agents to Inorganic Supports," Applied Biochemistry and Biotechnology, vol. 41, pp. 157-188, 1993, published by Humana Press Inc. (Totowa, NJ).

Kuby, J., Immunology, Second Edition (1994), pp. 147-150, W.H. Freeman and Company (New York, NY).

Drawhorn, R.A. et al., "Anchoring of Nematic Liquid Crystals on Self-Assembled Monolayers Formed from Alkanethiols on Semi-transparent Films of Gold," J. Phys. Chem. vol. 99, pp. 16511-16515, 1995, published by the American Chemical Society (Washington, D.C.).

Gupta, V.K. et al., "Uniform Anchoring of Nematic Liquid Crystals on Self-Assembled Monolayers Formed from Alkanethiols on Obliquely Deposited Films of Gold," Langmuir, vol. 12, pp. 2587-2593, 1996, published by American Chemical Society (Washington, D.C.).

Gupta, V.K. et al., "Azimuthal Anchoring Transition of Nematic Liquid Crystals on Self-Assembled Monolayers Formed from Odd and Even Alkanethiols," Physical Review E, vol. 54, No. 5, pp. R4540-R4543, Nov. 1996, published by the American Physical Society (Washington, D.C.).

Yang, H.C. et al., "Molecular Interactions between Organized, Surface-Confined Monolayers and Vapor-Phase Probe Molecules. 8. Reactions between Acid-Terminated Self-Assembled Monolayers and Vapor-Phase Bases," Langmuir, vol. 12, pp. 726-735, 1996, published by American Chemical Society (Washington, D.C.).

Gallardo, B.S. et al., "Ferrocenyl Surfactants at the Surface of Water: Principles for Active Control of Interfacial Properties," Langmuir, vol. 12, pp. 4116-4124, 1996, published by the American Chemical Society (Washington, D.C.).

Cornell, B.A. et al., "A Biosensor that uses Ion-Channel Switches," Nature, vol. 387, pp. 580-583, Jun. 5, 1997, published by Nature Publishing (New York, NY).

Lin, V. et al., "A Porous Silicon-Based Optical Interferometric Biosensor," Science, vol. 278, pp. 840-843, Oct. 31, 1997, published by the American Association for the Advancement of Science (Washington, D.C.).

Pan, J.J. et al., Molecular Recognition and Colorimetric Detection of Cholera Toxin by Poly(diacetylene) Liposomes Incorporating Gm1 Ganglioside, Langmuir, vol. 13, No. 6, pp. 1365-1367, 1997, published by the American Chemical Society (Washington, D.C).

Delamarche, E. et al., "Patterned Delivery of Immunoglobulins to Surfaces Using Microfluidic Networks," Science, vol. 276, pp. 779-781, May 2, 1997, published by the American Association for the Advancement of Science (Washington, D.C.).

Gupta, V.K. et al., "Optical Amplification of Ligand-Receptor Binding Using Liquid Crystals," Science, vol. 279, pp. 2077-2080, Mar. 27, 1998, published by the American Association for the Advancement of Science (Washington, D. C).

Ricco, A.J., "Surface Acoustic Wave Chemical Sensor Arrays: New Chemically Sensitive Interfaces Combined with Novel Cluster Analysis to Detect Volatile Organic Compounds and Mixtures," Acc. Chem. Res., vol. 31, pp. 289-296, 1998, published by American Chemical Society (Washington, D.C.).

Crooks, R. M. et al., "New Organic Materials Suitable for Use in Chemical Sensor Arrays," Acc. Chem. Res., vol. 31, pp. 219-227, 1998, published by American Chemical Society (Washington, D.C.).

Xia Y.N. et al., "Soft Lithography," Angew. Chem. Int. Ed., vol. 37, pp. 551-575, 1998, published by Wiley Interscience (Germany).

Dancil, K.S. et al., "A Porous Silicon Optical Biosensor: Detection of Reversible Binding of IgG to a Protein A-Modified Surface," J. Am. Chem. Soc., vol. 121 pp. 7925-7930, 1999, published by the American Chemical Society (Washington, D.C.).

Naoka, M. et al., "Ferroelectric Liquid Crystal Alignment Films Utilizing Poly (DL amino acids) and Fibrous Proteins," Kobunshi Ronbunshu, vol. 56, No. 6, pp. 396-400, Jun. 1999.

Skaife, J.J. et al., "Quantitative Characterization of Obliquely Deposited Substrates of Gold by Atomic Force Microscopy: Influence of Substrate Topography on Anchoring of Liquid Crystals," Chem. Mater., vol. 11, pp. 612-623, 1999, published by American Chemical Society (Washington, D.C.).

Shah, R.R. et al., "Using Liquid Crystals to Image Reactants and Products of Acid-Base Reactions on Surfaces with Micrometer Resolution," J. Am. Chem. Soc., vol. 121, pp. 11300-11310, 1999, published by American Chemical Society (Washington, D.C.).

Kim, S-R. et al., "Orientation of Liquid Crystals on Mechanically Rubbed Films of Bovine Serum Albumin: A Possible Substrate for Bimolecular Assays Based on Liquid Crystals," Anal. Chem., vol. 72, No. 19, pp. 4646-4653, Oct. 1, 2000, published by the American Chemical Society (Washington, D.C.).

Power Point presentation regarding "Optical Detection and Amplification of Bimolecular Interactions Using Liquid Crystals", by Jeff Brake and Nicholas Abbott, dated Apr. 26, 2000. Presented at the University of Wisconsin-Madison, Madison, Wisconsin, on April 26, 2000.

Niculescu, M. et al., "Redox Hydrogel-Based Amperometric Bienzyme Electrodes for Fish Freshness Monitoring," Anal. Chem., vol. 72, pp. 1591-1597, 2000, published by American Chemical Society (Washington, D.C.).

Shah, R.R. et al., "Coupling of the Orientations of Liquid Crystals to Electrical Double Layers Formed by the Dissociation of Surface-Immobilized Salts," J. Phys. Chem. B., vol. 105, pp. 4936-4950, 2001, published by American Chemical Society (Washington, D.C.).

Abbott, N.L. et al., "Imaging of Adsorption and Self-Organization of Amphiphiles at Aqueous-Liquid Crystals Interfaces," American Chemical Society Book of Abstracts, 221st National Meeting, Apr. 1-5, 2001.

* cited by examiner

DETECTING INTERACTIONS AT BIOMIMETIC INTERFACES WITH LIQUID CRYSTALS

CROSS REFERENCE TO RELATED APPLICATION

This application is a divisional of U.S. patent application Ser. No. 11/523,319, filed on Sep. 19, 2006, which is a divisional of U.S. patent application Ser. No. 10/119,648, filed Apr. 10, 2002, now U.S. Pat. No. 7,125,592, both of which are incorporated herein by reference in their entirety.

GOVERNMENT RIGHTS

This invention was made with United States government support awarded by the following agency: NAVY N00014-99-1-0250. The United States government has certain rights in this invention.

FIELD OF THE INVENTION

The invention relates generally to methods and devices for detecting interactions of compounds with liquid crystals or with receptor molecules adsorbed on liquid crystals at liquid crystal/aqueous interfaces. The invention also relates to the detection of chemical reactions that occur at liquid crystal-aqueous interfaces.

BACKGROUND OF THE INVENTION

It is well known that phospholipids are a major component of cell membranes. It is also known that phospholipids form bilayers in cell membranes in which the hydrophilic heads of the phospholipids face outwards towards the exterior walls of the membrane and the hydrophobic tails face inwards. Other components in cell membranes include transmembrane proteins and cholesterol. Detection of interactions between analytes and cell membrane components is an area of continuous development as such interactions are critical to understanding cell signaling and transduction processes. Detection of such interactions may thus be used in screening modulators of signal transduction processes and for use in screening pharmaceutical activity.

Although many conventional assay methods work very well to detect the presence of target species, such methods are generally expensive and often require instrumentation and highly trained individuals, which makes them difficult to use routinely in the field. Furthermore, most commonly available assay methods do not provide information regarding interactions that occur at cell membranes or biomimetic interfaces. Thus, a need exists for assay devices and methods which are easy to use and detect interactions of analytes at interfaces that mimic those that occur at the external surface of cell membranes.

Recently, assay devices that employ liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B.; Abbott N. L. *Science*, 279, (1998), pp. 2077-2079. In addition, PCT publication WO 99/63329 published on Dec. 9, 1999, discloses assay devices using SAMs attached to a substrate and liquid crystal layer that is anchored by the SAM.

Although various methods have been reported for detecting target species in a sample, there are few methods which may be used to investigate interactions at interfacial membranes that mimic cell membranes. Therefore, a need exits for liquid crystal devices and methods which allow interactions of analytes at liquid crystal/aqueous interfaces that mimic cell membranes to be detected and amplified.

SUMMARY OF THE INVENTION

The present invention provides devices and methods for detecting interactions at interfaces between liquid crystals and aqueous solutions.

The invention provides a method of forming a liquid crystal device. In one aspect of the invention, the method includes contacting an aqueous solution that includes a surfactant and a receptor molecule with a top surface of a liquid crystal. The liquid crystal is in a holding compartment of a substrate, and the receptor molecule is adsorbed on the top surface of the liquid crystal upon contact with the aqueous solution and forms an interface between the liquid crystal and the aqueous solution. The receptor molecule is different than the surfactant.

In one embodiment, the surfactant is selected from a group that includes non-ionic surfactants, ionic surfactants, zwitterionic surfactants, polymeric surfactants, and polymers. In other embodiments, the surfactant is a quaternary ammonium compound such as cetyltrimethlammonium bromide or dodecyltrimethylammonium bromide. In still other embodiments, the surfactant has a critical aggregation concentration that is greater than 1 nM.

In some embodiments, the substrate includes a grid disposed on a support that is formed from a polymer or disposed on a support that includes a hydrophobic glass surface. In such embodiments, the grid defines a cavity comprising the holding compartment of the substrate. In some embodiments in which the grid is disposed on a hydrophobic glass surface, the method further includes treating a glass support with a hydrophobic treating agent to form the hydrophobic glass surface of the glass support. In still other such embodiments, the hydrophobic treating agent is an organosilicon compound such as octadecyltrichlorosilane. In some embodiments in which the grid is disposed on the hydrophobic glass surface, the method further includes depositing a metal such as gold or silver on a surface of a glass support to provide a metallized top surface and treating the metallized top surface with an organosulfur compound to form the hydrophobic glass surface of the support.

In other embodiments, the substrate includes a support with a top surface that defines at least one depression which comprises the holding compartment of the substrate. In other such embodiments, the support comprises a polymer or glass treated with a hydrophobic treating agent such that the top surface of the glass and at least one depression comprises a hydrophobic surface. In still other such embodiments the glass is treated with an organosilicon compound such as octadecyltricholorosilane to provide the hydrophobic surface. In still other such embodiments, the support is formed from glass and the method further includes depositing a metal such as gold or silver on the top surface of the glass to provide a metallized top surface and treating the metallized top surface with an organosulfur compound to form a hydrophobic top surface of the glass.

In yet other embodiments, the receptor molecule is a phospholipid. In some such embodiments, the phospholipid is present in the aqueous solution in the form of vesicles. In various embodiments, the phospholipid is selected from dilaurylphosphatidyl choline, dipalmitoylphosphatidyl choline, dilaurylphosphatidyl ethanolamine, dipalmitoylphosphatidyl ethanolamine, and combinations of these.

In various embodiments of the method of forming a liquid crystal device, the concentration of the receptor molecule in the aqueous solution ranges from 1 fM to 100 mM. In other such embodiments, the concentration of the receptor molecule ranges from 1 µM to 1 mM. In still other such embodiments, the concentration of the receptor molecule is about 0.1 mM.

In further embodiments of the method of forming a liquid crystal device, the receptor molecule adsorbed on the top surface of the liquid crystal is contacted with an aqueous solution free of the surfactant and the receptor molecule after the top surface of the liquid crystal has been contacted with the aqueous solution that includes the surfactant and the receptor molecule.

In various embodiments of the method of forming a liquid crystal device, the liquid crystal is a thermotropic, smectic, nematic, or cholesteric liquid crystal. In other embodiments, the liquid crystal is 4-cyano-4'-pentylbiphenyl.

In another embodiment of the method of forming a liquid crystal device, the substrate comprises a plurality of holding compartments, and the liquid crystal is in at least two different holding compartments of the substrate.

The invention also provides a method of detecting a compound in a flowing stream. The method includes passing an aqueous solution over the top surface of a liquid crystal located in a holding compartment of a substrate. The method also includes determining whether any change in the orientation of the liquid crystal occurs as the aqueous solution is passed over the top surface of the liquid crystal. The presence of the compound in the flowing stream is indicated by a change in the orientation of the liquid crystal.

In one embodiment of the method for detecting the presence of a compound in a flowing stream, a receptor molecule is adsorbed on the top surface of the liquid crystal and the aqueous solution is passed over the top surface of the receptor molecule. In such embodiments, the presence of a compound that interacts with the receptor molecule is indicated by a change in the orientation of the liquid crystal.

In one embodiment of the method for detecting the presence of a compound in a flowing stream, the substrate includes a plurality of holding compartments. In some such embodiments, the liquid crystal is located in at least two different holding compartments. In some such embodiments, a first receptor molecule is adsorbed on a top surface a liquid crystal in a first holding compartment and a second receptor molecule is adsorbed on the top surface of a liquid crystal in a second holding compartment. In such embodiments, the presence of different compounds in a flowing stream may be determined using the liquid crystal device.

In other embodiments of the method for detecting a compound in a flowing stream, the receptor molecule is a phospholipid whereas in other embodiments the phospholipid is selected from dilaurylphosphatidyl choline, dipalmitoylphosphatidyl choline, dilaurylphosphatidyl ethanolamine, dipalmitoylphosphatidyl ethanolamine, and combinations of these.

In various embodiments of the method of detecting a compound in a flowing stream, the compound is a protein while in other such embodiments, the compound is an enzyme such as, in one embodiment, a phospholipase.

In other embodiments of the method of detecting a compound in a flowing stream, the substrate includes a grid disposed on a hydrophobic surface of a glass support, and the grid defines a cavity that is the holding compartment of the substrate. In other embodiments, the substrate includes a support with a top surface that defines at least one depression which comprises the holding compartment of the substrate.

In some embodiments of the method of detecting a compound in a flowing stream, the compound is a surface-active compound. In such embodiments, the change in the orientation of the liquid crystal occurs as the surface-active compound is adsorbed on the top surface of the liquid crystal.

The invention also provides a liquid crystal device. The device includes a container having an inlet and an outlet, and a substrate that is disposed within the container. The inlet and outlet allow a solution to be passed through the device. The substrate includes at least one holding compartment and a liquid crystal located within the at least one holding compartment of the substrate. In some embodiments, the device further includes a receptor molecule adsorbed on the top surface of the liquid crystal.

In one embodiment of the liquid crystal device, the substrate includes a grid disposed on a support that comprises a polymer or a hydrophobic glass surface. In such embodiments, the grid defines a cavity comprising the at least one holding compartment of the substrate. In some such embodiments, the grid is disposed on the hydrophobic glass surface, and the hydrophobic glass surface comprises glass treated with an organosilicon compound. In other such embodiments, the grid is disposed on the hydrophobic glass surface, and the hydrophobic glass surface comprises an organosulfur compound bonded to a metallized top surface of a glass support. In some such embodiments, the metallized top surface comprises a gold or silver surface.

In other embodiments of the liquid crystal device, the substrate includes a support with a top surface that defines at least one depression that comprises the at least one holding compartment of the substrate. In some such embodiments, the support comprises a polymer or comprises a glass support with a hydrophobic glass surface. In some embodiments, the support comprises a glass support with a hydrophobic glass surface that includes glass treated with an organosilicon compound. In other embodiments, the support comprises a glass support with a hydrophobic glass surface that includes an organosulfur compound bonded to a metallized top surface of the glass support. In some such embodiments, the metallized top surface of the glass support comprises a gold surface or a silver surface.

Another aspect of the invention provides a method for determining a change in the oxidation state of a molecule adsorbed on a liquid crystal. The method includes contacting a liquid crystal device immersed in an aqueous solution with an oxidizing agent, a reducing agent, an applied oxidizing potential, or an applied reducing potential. The liquid crystal device includes a molecule that is adsorbed on a top surface of a liquid crystal located in a holding compartment of a substrate. The molecule includes a group that may be oxidized or reduced. The method also includes determining whether a change in the orientation of the liquid crystal occurs when the liquid crystal device is contacted with the oxidizing agent, the reducing agent, the applied oxidizing potential, or the applied reducing potential. A change in the orientation of the liquid crystal upon contact with the oxidizing agent, the reducing agent, the applied oxidizing potential, or the applied reducing potential indicates a change in the oxidation state of the molecule.

In one embodiment of the method for determining a change in the oxidation state of a molecule adsorbed on a liquid crystal, the molecule has a ferrocene group. In one such embodiment, the molecule is a (ferrocenylalkyl)trialkylammonium halide such as 11-(ferrocenyl-undecyl)trimethylammonium bromide.

In other embodiments of the method for determining a change in the oxidation state of a molecule adsorbed on a liquid crystal, the aqueous solution includes a quaternary ammonium compound such as cetyltrimethylammonium bromide or dodecyltrimethylammonium bromide.

In another aspect, the invention provides a method of forming a liquid crystal device. The method includes contacting an aqueous solution with a top surface of a liquid crystal solution comprising a liquid crystal and a surface-active compound dispersed or dissolved therein. The liquid crystal is located in a holding compartment of a substrate, and the surface-active compound migrates to the top surface of the liquid crystal solution upon contact with the aqueous solution forming an interfacial layer between the liquid crystal and the aqueous solution.

In one embodiment of the method of preparing a liquid crystal device in which the surface-active compound is dissolved or dispersed in the liquid crystal solution, the liquid crystal is 4-cyano-4'-pentylbiphenyl.

In other embodiments of the method of preparing a liquid crystal device in which the surface-active compound is dissolved or dispersed in the liquid crystal solution, the surface-active compound is a phospholipid such as dilaurylphosphatidyl choline, dipalmitoylphosphatidyl choline, dilaurylphosphatidyl ethanolamine, and dipalmitoylphosphatidyl ethanolamine.

In yet other embodiments of the method of preparing a liquid crystal device in which the surface-active compound is dissolved or dispersed in the liquid crystal solution, the substrate comprises a grid that is disposed on a hydrophobic surface of a glass support, and the grid defines a cavity that comprises the holding compartment of the substrate.

In still another embodiment of the method of preparing a liquid crystal device in which the surface-active compound is dissolved or dispersed in the liquid crystal solution, the substrate comprises a support with a top surface that defines at least one depression which comprises the holding compartment of the substrate.

In another aspect, the invention provides a method for detecting the binding of a compound to a receptor molecule. The method includes contacting an aqueous solution comprising a compound with a receptor molecule that is disposed on a top surface of a liquid crystal in a holding compartment of a substrate; and determining whether a change in the orientation of the liquid crystal occurs as the aqueous solution contacts the receptor molecule. A change in the orientation of the liquid crystal indicates the binding of the compound to the receptor molecule.

In one embodiment of the method for detecting the binding of a compound to a receptor molecule, the receptor molecule is a phospholipid such as a phospholipid selected from dilaurylphosphatidyl choline, dipalmitoylphosphatidyl choline, dilaurylphosphatidyl ethanolamine, dipalmitoylphosphatidyl ethanolamine, or combinations of these.

In other embodiments of the method for detecting the binding of a compound to a receptor molecule, the compound is a protein. In some such embodiments, the protein is an enzyme such as, in one embodiment, a phospholipase such as $PLA_2$.

In still other embodiments of the method for detecting the binding of a compound to a receptor molecule, the substrate includes a support with a top surface that defines at least one depression which comprises the holding compartment of the substrate.

In yet other embodiments of the method for detecting the binding of a compound to a receptor molecule, the substrate comprises a grid disposed on a hydrophobic surface of a glass support and the grid defines a cavity comprising the holding compartment of the substrate.

In still further embodiments of the method for detecting the binding of a compound to a receptor molecule, the substrate comprises a plurality of holding compartments. In some such embodiments, a first receptor molecule is adsorbed on the top surface of a liquid crystal in a first holding compartment and a second receptor molecule is adsorbed on the top surface of a liquid crystal in a second holding compartment.

In still further embodiments of the method for detecting the binding of a compound to a receptor molecule, the compound that binds to the receptor molecule does not undergo a chemical reaction with the receptor molecule.

The invention further provides a liquid crystal device prepared according to the methods of the present invention.

Further objects, features and advantages of the invention will be apparent from the following detailed description when taken in conjunction with the accompanying drawings.

BRIEF DESCRIPTION OF THE DRAWINGS

FIG. 1A is a glass slide. FIG. 1B is the glass slide after it has been treated with a material such as OTS. FIG. 1C shows a treated glass slide with a copper TEM grid placed on the top surface of the slide with approximately 1 µL of a liquid crystal added by syringe to the grid. FIG. 1D shows a 25 µL capillary tube being used to remove excess liquid crystal from a TEM grid. FIG. 1E is a scanned image showing a slide with several TEM grids held in place in an aqueous solution in a glass dish with binder clips.

FIG. 5B, 1 µM DLPC for 2 hours; FIG. 5C, 10 µM DLPC for 5 minutes; FIG. 5D 10 µM DLPC for 2 hours; FIG. 5E, 100 µM DLPC for 5 minutes).

FIGS. 10A and 10D are scanned images of the optical texture after a 90 minute exposure to a 1 nM PLA$_2$, Tris-buffered 5 mM CaCl$_2$ aqueous solution. FIGS. 10B and 10F are scanned images of the optical texture after a 90 minute exposure to a 100 nM PLA$_2$. Tris-buffered 5 mM CaCl$_2$ aqueous solution. FIGS. 10C and 10F are scanned images of the optical texture after a 90 minute exposure to a 100 nM PLA$_2$, 5 mM EDTA, Tris-buffered aqueous solution.

DETAILED DESCRIPTION OF THE INVENTION

Figure 1A:
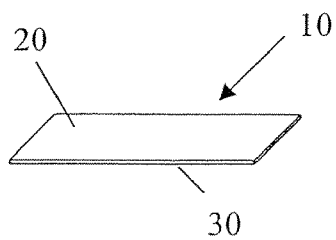
FIGS. 1A-1E show various steps used to prepare a liquid crystal device according to a first embodiment.

The term "TEM" refers to transmission electron microscopy.

The term "OTS" refers to octadecyltrichlorosilane, an organosilicon compound of formula $CH_3(CH_2)_{17}SiCl_3$.

The term "5CB" refers to the liquid crystal 4-cyano-4'-pentylbiphenyl.

The term "DPPC" refers to dipalmitoylphosphatidyl choline, a compound having the structure I where $R^1$ is a —$(CH_2)_{14}CH_3$ group.

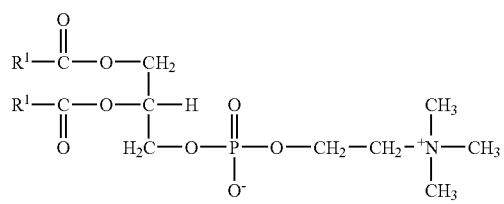

I

The term "DLPC" refers to dilaurylphosphatidyl choline, a compound having the structure I where $R^1$ is a —$(CH_2)_{10}Ch_3$ group.

The term "DPPE" refers to dipalmitoylphosphatidyl ethanolamine, a compound of structure II where $R^1$ is a —$(CH_2)_{14}Ch_3$ group.

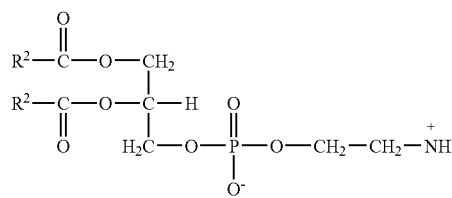

II

The term "DLPE" refers to dilaurylphosphatidyl ethanolamine, a compound of structure II where $R_2$ is a —$(CH_2)_{10}Ch_3$ group.

The term "PLA$_2$" refers to the enzyme phospholipase A$_2$.

The term "LLPC" refers to lauryllysophosphatidyl choline. Lauric acid and LLPC are the enzymatic products produced by the reaction of activated PLA$_2$ and DLPC where one of the lauric acid groups is cleaved from the DLPC. LLPC has the structure III where $R^3$ is a —$(CH_2)_{10}CH_3$ group.

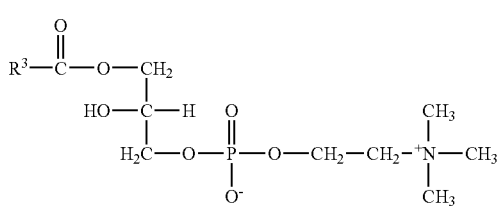

The term "CTAB" refers to cetyltrimethylammonium bromide, a quaternary ammonium surfactant compound having the formula $[CH_3(CH_2)_{15}N(CH_3)_3]^+Br^-$.

The term "DTAB" refers to dodecyltrimethylammonium bromide, a quaternary ammonium surfactant compound having the formula $[CH_3(CH_2)_{11}N(CH_3)_3]+Br—$.

The term "DBTAB" refers to dodecyl-1,12-bis(trimethylammonium) bromide, a surfactant having the formula $[(CH_3)_3N+(CH_2)_{12}N+(CH_3)_3]2\ Br^-$.

The term "HTAB" refers to 11-hydroxyundecyltrimethyl ammonium bromide, a surfactant.

The term "FTMA" refers to 11-(ferrocenylundecyl)trimethyl-ammonium bromide, a surfactant with an oxidizable ferrocene group.

The term "BSA" refers to bovine serum albumin.

The term "Tris" refers to a buffering solution containing 10 mM tris(hydroxymethyl)aminomethane, a buffering compound of formula $(HOCH_2)_3CNH_2$, and 100 mM of sodium chloride.

The term "EDTA" refers to ethylenediaminetetraacetic acid, a compound having the formula $(HO_2CCH_2)_2NCH_2CH_2N(CH_2CO_2H)_2$ and metal chelating properties.

The term "SDS" refers to sodium dodecyl sulfate, a surfactant compound having the formula $CH_3(CH_2)_{11}OSO_3^-\ Na^+$.

All ranges recited herein include all combinations and subcombinations included within that range's limits. For example, a range of from about 0.2 μm to about 1 cm includes ranges of from 20 μm to 1 cm, of from 20 μm to 5,000 μm, of from 30 μm to 1 cm, of from 25 μm to 600 μm, of from 25 μm to 5,000 μm, of from 50 μm to 1 cm, of from 50 μm to 600 μm, of from 100 μm to 1 cm, of from 100 μm to 600 μm, and measurements of and about 20 μm, of and about 50 μm, of and about 100 μm, of and about 500 μm, of and about 5,000 μm, and of and about 1 cm etc. Furthermore, one skilled in the art will recognize that any listed range can be easily recognized as sufficiently describing and enabling the same range being broken down into at least equal halves, thirds, quarters, fifths, tenths, etc. As non-limiting examples, each range discussed herein can be readily broken down into a lower third, middle third, and upper third, and can be broken down into a lower half and an upper half.

Generally, the invention provides liquid crystal devices and methods for detecting interactions between a compound in an aqueous solution and a liquid crystal in a holding compartment of a substrate. When a solution containing the compound is passed over the top of the liquid crystal, a change in the orientation of the underlying liquid crystal is observed indicating the presence of the compound in the aqueous solution. A change in the orientation of the liquid crystal may indicate binding of the compound to the liquid crystal or may indicate the binding of the compound to a receptor molecule disposed on the top surface of the liquid crystal. A change in the orientation of the liquid crystal may also indicate that a chemical reaction between the compound and the liquid crystal or between the compound and a receptor molecule adsorbed on the top surface of the liquid crystal has occurred. Further, a change in the orientation of the liquid crystal may indicate the desorption of all or part of a receptor molecule. If part of the receptor molecule desorbs, it may be fragmented through a chemical reaction such as, but not limited to, hydrolysis, oxidation or reduction or enzymatic cleavage. Part or all of the receptor may also desorb because it binds to a species that is present in a solution that contacts the liquid crystal. In some embodiments, a receptor molecule is adsorbed on the top surface of the liquid crystal and the aqueous solution is passed over the top surface of the receptor molecule. The presence of a compound that interacts with (binds to or reacts with) the receptor molecule is indicated by the change in the orientation of the liquid crystal. In one embodiment, a method of forming a liquid crystal device includes contacting an aqueous solution that includes a surfactant and a receptor molecule with a top surface of a liquid crystal in a holding compartment of a substrate. The receptor molecule is adsorbed on the top surface of the liquid crystal as it contacts the aqueous solution forming an interfacial membrane between the liquid crystal and the aqueous solution.

Phospholipids such as dialkylphosphatidyl cholines and dialkylphosphatidyl ethanolamines such as DLPC, DPPC, DPPE, and DLPE may be used to form an interfacial membrane between the liquid crystal and an aqueous solution in one aspect of the invention. Other suitable phospholipids include dialkenylphosphatidyl cholines and ethanolamines and phosphatidyl cholines and ethanolamines where one fatty acid group is an alkyl group and one fatty acid group is an alkenyl group. Because phospholipids are major components in cell membranes, interfacial membranes prepared from such receptor species act as biomimetic membranes, and they may be used to explore and evaluate interactions at cell membranes including binding and chemical reactions. When transmembrane proteins are additionally present in such interfacial membranes, the devices of the present invention allow for exploration and detection of cell signaling and other processes.

Substrates suitable for use in preparing liquid crystal devices of the present invention include a holding compartment into which a liquid crystal is placed. In some embodiments, the substrate includes a support with a top surface defining depressions such as wells or troughs into which the liquid crystal may be deposited (See FIG. 2) while in other embodiments the substrate includes a support with a top surface in combination with a grid or other suitable device for holding the liquid crystal (See FIGS. 1C-1E). Those skilled in the art will recognize that substrates with other configurations may be utilized in practicing the present invention.

A wide variety of materials may be employed as supports in the substrates of the present invention as will be apparent to those skilled in the art. For example, suitable substrates include supports made of polymers, metals, metal oxides, and silica-containing materials such as glass, silica, and quartz. Examples of polymeric supports include, but are not limited to, polystyrene, polycarbonates, polyurethanes, polyolefins such as polyethylene and polypropylene, and polyalkyl acrylates and/or methacrylates such as poly(methyl methacrylate). Examples of metals suitable for use as supports include, but are not limited to, copper, silver, gold, aluminum, platinum, nickel, and stainless steel. Examples of metal oxides suitable for use as supports include, but are not limited to, indium oxide, tin oxide, aluminum oxide, magnesium oxide, and indium-tin oxide. Suitable supports may also be made from materials that include glass, quartz, and silica. Glass slides, glass plates, and silica wafers are utilized as supports in various embodiments of the invention. Preferably, supports are cleaned prior to use. For example, glass slides and glass plates may be cleaned by treatment in "piranha solution" (70% $H_2SO_4$/30% $H_2O_2$) for 1 hour and then rinsing with deionized water before drying under a stream of nitrogen. "Piranha solution" requires care in handling as it reacts violently with organic compounds and should not be stored in closed containers.

Supports with surfaces that are hydrophilic in nature such as glass, silica, and quartz are preferably treated with a hydrophobic treating agent that converts such surfaces into hydrophobic surfaces. Such treatment provides for better adhesion between the liquid crystal and the support when immersed in water. Various organosilicon compounds will react with hydroxyl groups on the surface of dried glass, aluminum oxide, and/or silica to create suitable hydrophobic surfaces for the substrate. Examples of organosilicon compounds that may be used to treat a glass support to form a hydrophobic glass surface include, but are not limited to, perfluorinated silanes, alkyltrichlorosilanes, and alkoxysilanes. In one embodiment, a clean and dry glass slide is treated with an organotrihalosilane such as OTS to provide a support with a suitable hydrophobic surface for use in the present invention. In other embodiments, glass supports such as glass slides or glass plates are coated with a metal such as gold or silver and functionalized by reaction with an organosulfur compound such as, but not limited to, alkanethiols, hydroxyalkanethiols, and/or carboxyalkanethiols. In other embodiments, glass supports are treated with a polymeric materials such as, but not limited to polyalkyloxides via surface-initiated polymerization. In yet other embodiments, a glass support may be immersed in a protein solution such as, but not limited to, a bovine serum albumin solution or surfactant solution such as, but not limited to, a solution of DLPC, DPPC, CTAB, or SDS. After immersion in a protein or surfactant solution, a glass support such as a glass slide is typically removed and then dried.

As noted above, suitable substrates for employment in the present invention include supports with surfaces defining at least one depression such as a well into which liquid crystal may be placed. Suitable substrates also include supports that need not include any depressions when used in combination with a grid or other device for holding the liquid crystal. In embodiments in which a support is used in combination with a grid or other device that holds the liquid crystal, the grid typically defines a cavity with dimensions of from 0.2 μm to 1 cm from one side to the other and from 0.1 μm to 200 μm in depth. The particular shape of the cavity is not critical to the invention. For example, the cavity may be circular, square, rectangular, pentagonal, hexagonal, heptagonal, or octagonal in shape. Suitable side to side dimensions in various embodiments range from about 0.2 μm to about 1 cm, from 0.2 μm to 5,000 μm, from 30 μm to 1 cm, from 25 μm to 600 μm, from 25 μm to 5,000 μm, from 50 μm to 1 cm, from 50 μm to 600 μm, from 100 μm to 1 cm, from 100 μm to 600 μm, and include dimensions of and about 0.2 μm, of and about 2 μm, of and about 20 μm, of and about 50 μm, of and about 100 μm, of and about 200 μm, of and about 300 μm, of and about 500 μm, of and about 5,000 μm, and of and about 1 cm. In one embodiment, TEM grids have been found particularly suitable for use in preparing substrates in combination with OTS treated glass slides and glass plates as shown in FIGS. 1A-1E.

Figure 1B:
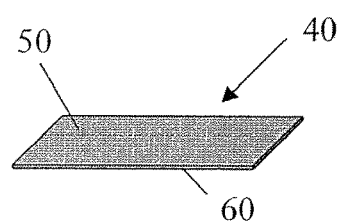
Figure 1C:
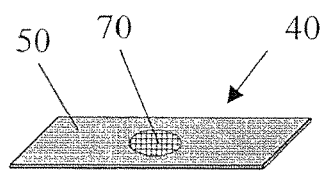
Figure 1D:
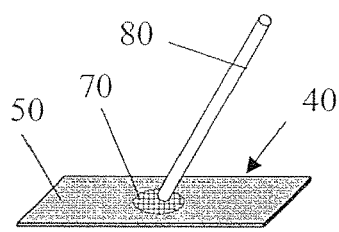
Figure 1E:
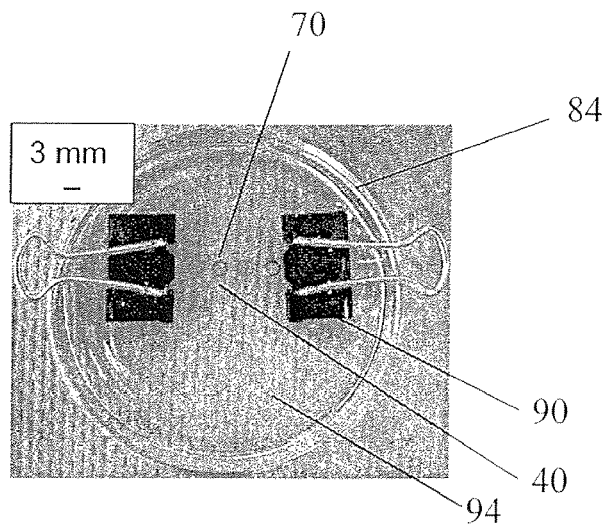

FIGS. 1A-1E show various stages in the preparation of a liquid crystal device according to one embodiment of the invention. As shown in FIGS. 1A and 1B, a clean and dry glass slide 10 having a top surface 20 and a bottom surface 30 may be treated with a compound such as octadecyltrichlorosilane (OTS) to provide a treated glass slide 40 with a hydrophobic surface having a hydrophobic top surface 50 and a hydrophobic bottom surface 60. This may be accomplished by immersing the glass slide in a hydrocarbon solution containing a hydrophobic, treating agent such as a dry heptane or hexane solution with OTS. Using one alternative procedure, a top surface 20 of a suitable clean glass slide 10 may be treated with a hydrophobic agent so that only top surface 20 of slide 10 is treated to prepare a treated glass slide 40 with a hydrophobic top surface 50 and an untreated hydrophilic bottom surface. Following reaction with a hydrophobic treating agent, a treated glass slide 40 is typically rinsed in a solvent such as an alcohol such as, but not limited to, ethanol or methanol, and then dried such as under an inert gas stream. As shown in FIG. 1C, according to one embodiment, one or more transmission electron microscopy (TEM) grid(s) 70 placed on hydrophobic top surface 50 of treated glass slide 40 provides a substrate with holding areas into which a liquid crystal such as 5CB may be deposited using any suitable means. As shown in FIG. 1D, excess liquid crystal may be removed from TEM grid 70 using a capillary tube 80. In just one embodiment such as that shown in FIG. 1E, a treated glass slide 40 with several TEM grids 70 containing liquid crystal may be placed in a glass dish 84 or other suitable container for holding an aqueous solution 94. The container may include two or more openings such an inlet and an outlet such that a solution may be pumped into and out of the container to provide a liquid crystal device for use with a flowing aqueous or other stream. The treated slide 40 may then optionally be secured in place using any suitable securing devices known to those skilled in the art such as binding clips 90. A suitable receptor such as, but not limited to a phospholipid such as, but not limited to, DPPC, DLPC, DPPE, and DLPE, in an aqueous solution may then be contacted with the top of the liquid crystal in a grid 70 on a treated slide 40 such that the receptor forms a boundary layer or interface of adsorbed receptor between the water and the top of the liquid crystal.

In one embodiment, a liquid crystal device of the invention includes a plurality of holding compartments. A liquid crystal may be deposited or placed into two or more of the holding compartments. A single receptor species may be adsorbed on the liquid crystal in two or more holding compartments to provide an array of interfacial membranes for use in detecting compounds in aqueous solution. In an alternative embodiment, one receptor species is adsorbed on a top surface of a liquid crystal in one holding compartment and a second receptor species is adsorbed on a top surface of a liquid crystal in a second holding compartment to provide a device that allows the detection of multiple compounds in an aqueous solution. Different species may be separately adsorbed at the liquid crystal-aqueous interface in different holding compartments by pipetting droplets of solution containing different receptors or other species over liquid crystal contained in two or more holding compartments. For example, in one embodiment, D-DPPC is adsorbed on the surface of 5CB located in one holding compartment in a TEM grid on an OTS-treated glass slide, and L-DPPC is adsorbed on the top surface of 5CB located in a second holding compartment in the TEM grid. The same method may be used when the holding compartment of the substrate is defined by wells or depressions formed in the top surface of the substrate.

Figure 2:
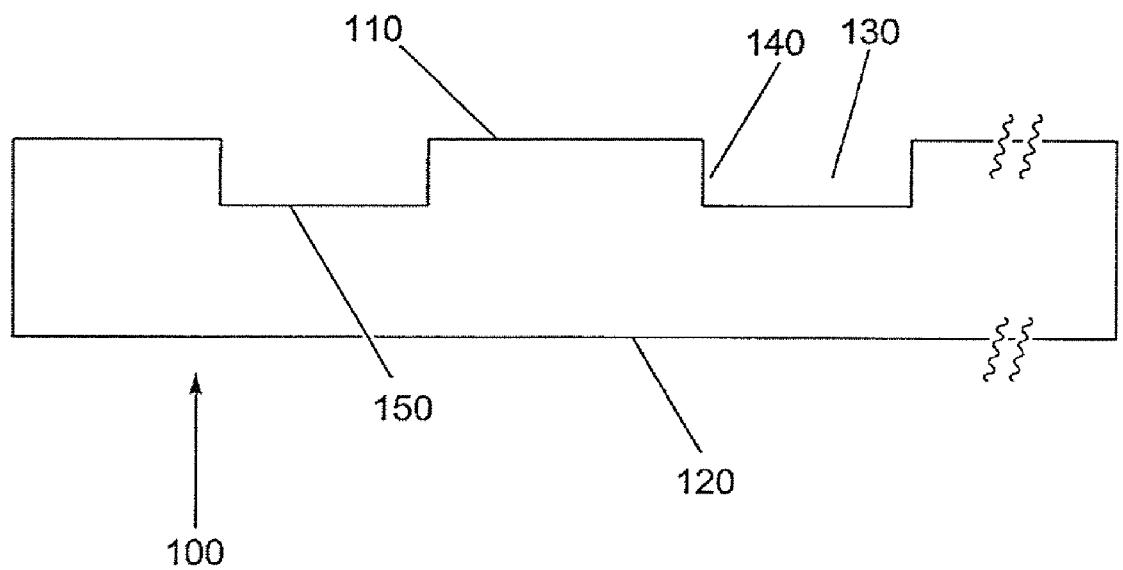
FIG. 2 is a cross-sectional side view of a portion of a substrate having a top surface that defines wells or troughs into which a liquid crystal may be placed.

A support with depressions for use as a substrate is shown in FIG. 2. Such supports may be molded to include depressions or the depressions may be formed in a top surface of the support. For example, suitable substrates include polymeric supports with wells that are molded in the top surface of the support. Suitable substrates also include those in which the depression is etched or cut into a top surface. For example, a glass surface containing depressions formed by etching may be treated with a hydrophobic treating agent such as OTS to make the surface hydrophobic and then filled with a liquid crystal in one aspect of the invention. Those reasonably skilled in the art, will understand that various supports defining depressions may be used in accordance with the present invention. Generally, the dimensions of the depressions in supports with surfaces defining depressions for holding a liquid crystal are similar to those of the grid in embodiments in which a grid is used in combination with a support to provide the substrate with a holding compartment into which the liquid crystal is placed. Thus, suitable side to side dimensions of wells in supports with depressions range from about 0.2 µm to about 1 cm, from 0.2 µm to 5,000 µm, from 30 µm to 1 cm, from 25 µm to 600 µm, from 25 µm to 5,000 µm, from 50 µm to 1 cm, from 50 µm to 600 µm, from 100 µm to 1 cm, from 100 µm to 600 µm, and include dimensions of and about 0.2 µm, of and about 2 µm, of and about 20 µm, of and about 50 µm, of and about 100 µm, of and about 200 µm, of and about 300 µm, of and about 500 µm, of and about 5,000 µm, and of and about 1 cm. The depressions typically have a depth of less than or about 200 µm.

A cross-sectional view of a substrate 100 with a support having depressions for holding a liquid crystal is shown in FIG. 2. Substrate 100 includes a top surface 110 and a bottom surface 120. Top surface 110 of substrate 100 is microtextured having wells or troughs 130 defined by side walls 140 and well bottom surfaces 150. An appropriate amount of a selected liquid crystal may be placed into the wells or troughs 130 of substrate 100. A substrate such as that shown in FIG. 2 that includes liquid crystal in the wells or troughs 130 may be placed in any suitable container for holding water such as, but not limited to, a glass dish and then exposed to vesicle solutions containing receptor molecules such as, but not limited to a solution containing DPPC. DLPC, DLPE, or DPPE vesicles, to form a device of the present invention.

Various liquid crystals may be employed in the devices and methods of the present invention. Examples of suitable liquid crystals, include, but are not limited to, 4-cyano-4'-pentylbiphenyl (5CB), 7CB, and 8CB. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Because the devices and methods of the present invention include contacting the liquid crystal with aqueous solutions, suitable liquid crystals employed in the invention should be insoluble in water or have very limited solubility in water. Additionally, suitable liquid crystals employed in the invention should not react with water. In one embodiment of the present invention, the liquid crystal deposited in the holding compartment of the substrate (in a grid cavity or in the depression in a support with a surface defining a depression) is 4-cyano-4'-pentylbiphenyl (5CB). Although various types of liquid crystal may be employed, nematic and thermotropic liquid crystals are preferred. However, smectic liquid crystals formed from 8CB are also suitable for use in the present invention. Suitable liquid crystals further include smectic C, smectic C*, blue phases, cholesteric phases, smectic A, and polymeric liquid crystals.

A liquid crystal may be placed in one or more grid(s) or depression(s) of a suitable substrate using various techniques. For example, a liquid crystal may be deposited in a grid or well using a microliter syringe. As described above and in the Examples, a microliter capillary tube may then be used to remove excess liquid crystal from the substrate surface. In one embodiment, a liquid crystal in a holding compartment of a substrate is heated into its isotropic phase at a temperature of about 50° C. and is then plunged into water at a temperature ranging from about 20° C. to 25° C. This methodology has been found effective at removing air bubbles and excess liquid crystal and for producing suitable liquid crystal devices ready for adsorption of a selected receptor molecule. As noted above, the liquid crystal is typically deposited into the grid or depression using a microliter syringe. The liquid crystal may also be deposited into the grid or depressions by first dissolving the liquid crystal in a volatile organic solvent such as hexane, pentane, heptane, methylene chloride, or chloroform, depositing an appropriate amount of the dissolved liquid crystal on the grid or depression, and allowing the solvent to evaporate leaving the liquid crystal in the grid. The liquid crystal may also be deposited in the grids or depressions using microfluidic channels placed over the patterned surface or grid. A liquid crystal may then be injected into the microfluidic channels and drawn into the grids or depressions by capillary action or pressure-driven flow.

Various receptor species may be used in accordance with one aspect of the present invention. The receptor species are adsorbed on the top surface of the liquid crystal and form an interfacial membrane between the liquid crystal and the aqueous phase. If an aqueous solution includes a sufficient amount of a compound that interacts with the receptor species, a change in the orientation of the liquid crystal will occur indicating the interaction (binding and/or chemical reaction) between the receptor species and the compound. Typically, the liquid crystal is viewed through polarized light to determine whether the orientation has been altered. In one embodiment, a polarized light microscope is used and may further be used in conjunction with cross polarizers. Examples of suitable receptor species include surfactants such as SDS, CT AB, and fatty acids, cholesterol, sphingomyelins, phosphatidylcholines, phosphatidylethanolamines, phosphatidylserines, inositol phospholipids, lysophospholipids, glycolipids (gangliosides), and membrane proteins. Other suitable receptor species include, but are not limited to, integral membrane proteins such as glycoproteins, cell signaling proteins such as G proteins, growth factor receptors, growth factors, ion channel proteins, proteoglycans, and integrins, and molecules not specifically membrane associated such as hormones (e.g. estrogen, testosterone, glucogons, and epinephrine), hormone receptor proteins, insulin, biotin, sugars (e.g. glucose, lactose), DNA, RNA, collagen, pharmaceuticals, enzyme inhibitors, peptides, polypeptides, nucleotides, oligonucleotides, antibodies, immunoglobulins, chelating agents, and metal ions tethered to a surfactant molecule. Such receptor species may be used alone or in combination to provide mixed membranes with more than one species. For example, DLPE and DLPC may be coadsorbed on the surface of a liquid crystal from an aqueous solution containing these receptor species to create a mixed membrane at the liquid/crystal water interface. In some embodiments, phospholipids such as phosphatidyl cholines (DPPC and DLPC) and phosphatidyl ethanolamines (DLPE and DPPE) may be adsorbed on the surface of the liquid crystal to prepare interfacial membranes that are biomimetic in nature and which may be used to simulate cell membranes.

Racemic mixtures and enantiomerically pure or enriched receptor species such as $_D$-DPPC and $_L$-DPPC may be adsorbed on liquid crystals such as 5CB to investigate interaction with and activity of analytes such as $PLA_2$ with the interfacial membranes. As explained in the following Examples, liquid crystal, devices of the present invention prepared from 5CB and $_D$-DPPC or $_L$-DPPC were used to show that while PLA2 binds to the surface of membranes formed from either enantiomer of DPPC, it only reacts with L-DPPC. Liquid crystal devices constructed from DLPC or DPPC and 5CB confined in TEM grids on OTS-treated glass supports were also used to demonstrate that Ca2+ ions are necessary for both the binding and catalytic activity of $PLA_2$.

In one embodiment, the invention provides a method for detecting the binding of a compound such, as but not limited to, a protein or enzyme such as a phospholipase like $PLA_2$ to a receptor molecule such as, but not limited to, a phospholipid such as DPPC, DLPC, DPPE, or DLPE. The method includes contacting an aqueous solution that includes the compound with a receptor molecule that is disposed on a top surface of a liquid crystal in a holding compartment of a substrate. The method further includes determining whether a change in the orientation of the liquid crystal occurs as the aqueous solution contacts the receptor molecule. A change in the orientation of the liquid crystal indicates the binding of the compound to the receptor molecule. Substrates which include a grid disposed on a support and those in which a top surface defines a depression may be used in accordance with the method. In some such methods, the compound binds to the receptor molecule but does not undergo a chemical reaction with the receptor. For example, the binding of activated $PLA_2$ to D-DPPC may be detected using this method even though D-DPPC does not react with the enzyme.

Protein receptor species may be included with phospholipids and adsorbed on liquid crystals. Biomimetic interfacial membranes prepared from such proteins and phospholipids provide liquid crystal devices that allow for analysis of cell signaling and transduction processes. Proteins may be integrated with lipids using any of several methods, including but not limited to, co-adsorption of mixtures including both lipids and protein, initial adsorption of protein from solution followed by exposure to and adsorption of lipids, and initial formation of lipid layers followed by exposure to the protein. Proteins may also be introduced into adsorbed layers of surfactants by tethering the molecule to a surfactant via chemistry with the headgroup (e.g. amine-carboxylic acid conjugation or disulfide linkage). In the latter method, the conjugated surfactant and pure surfactant are generally either sequentially or co-adsorbed at the desired molar ratio. Proteins may also be attached to the adsorbed layers by molecular recognition events such as a histidine/$Ni^{2+}$-NTA interaction. Examples of suitable proteins for employment as receptor molecules include RAS proteins such as farnesylated RAS, receptor tyrosine kinases, epidermal growth factor, insulin receptor, platelet-derived growth factor receptor, and fibroblast growth factor receptor. Other suitable proteins include integral membrane proteins such as glycoproteins, cell signaling proteins such as G proteins, ion channel proteins, proteoglycans, integrins, hormone receptor proteins, growth factors, enzyme inhibitors, enzymes, antibodies, and immunoglobulins. Those skilled in the art will recognize that various other proteins and receptor species may be used in accordance with the liquid crystal devices of the present invention. A liquid crystal device prepared using an appropriate receptor species may be used to detect bacteria, viruses, DNA, RNA, proteins, enzymes, ions, and cells in an aqueous solution that is circulated or passed over or contacted with the top of an interfacial membrane on a liquid crystal. In one embodiment, the components of a cell membrane are broken down and reconstituted on the top surface of a liquid crystal in a device of the present invention. In such embodiments, binding of a compound to a component of the cell membrane and/or chemical reaction with a component of the cell membrane is detected by a change in the orientation of the liquid crystal as the compound contacts the component of the cell membrane adsorbed on the top surface of the liquid crystal or the components of the membrane are desorbed from the interface between the LC and water upon interaction with the compound. For example, the chemical reaction between an enzyme such as $PLA_2$ and a phospholipid may be detected when the products of the chemical reaction desorb from the liquid crystal interface.

The receptor species are typically adsorbed on the surface of the liquid crystal from an aqueous solution. In one embodiment, vesicles of a phospholipid such as DLPC, DPPC, DLPE, DPPE, or combinations of these in an aqueous solution are contacted with a substrate that includes a liquid crystal in a grid or depression. This may be accomplished by immersing the substrate in an aqueous solution that includes the receptor species or by circulating the aqueous solution over the top of the liquid crystal for an appropriate length of time. Generally, the concentration of the receptor species in the aqueous or water solution ranges from 1 fM to 0.1 M. In other embodiments, the concentration of the receptor species ranges from 1 µM to 1 mM or is about 0.1 mM. Generally, the greater the concentration of the receptor species in the aqueous solution, the shorter will be the time required to form a suitable interfacial membrane. The amount of time required for interfacial membrane formation may also depend on the phase state (e.g. monomers, micelles, vesicles in the liquid state, vesicles in the gel state) of the receptor species in the aqueous solution. Vesicle solutions containing lipids and any lipid conjugated receptors are typically prepared by the following method. The lipids are first dissolved in an organic solvent such as chloroform and combined in mixtures to give the desired ratio of various lipids. The organic solvent is then evaporated under an inert gas and/or under vacuum. The dried lipid is resuspended in an aqueous solution containing the desired buffers at a given pH, The aqueous solution is typically buffered with buffer components including phosphates, Tris, acetates, HEPES, MOPS, calcium chloride, potassium chloride, sodium chloride, and EDTA at concentrations ranging from 1 µm to 1 M with a preferred range being 1 mM to 100 mM. The pH of the solution may range from 2-12, from 4-10, or from 6-9. The dried lipid mixture combined with the buffer is typically sonicated for 1 to 20 pulses of 1 to 600 seconds at a power of 10 to 100 watts. In one embodiment, the sonication method is 3 pulses for 300 seconds at a power of 15 watts. Finally, the solutions are filtered using 100-220 nm pore size membranes for 1-20 passes. In one embodiment, the sonicated solution is filtered once through a 220 nm pore size membrane.

As the receptor species are adsorbed on the surface of the liquid crystal, the optical appearance of the liquid crystal viewed through cross-polarizers changes from bright indicating planar alignment of the liquid crystal to dark indicating homeotropic alignment of the liquid crystal. In other embodiments of the invention, the adsorption of the receptor results in planar alignment of the liquid crystal, or a tilted alignment of the liquid crystal, or an alignment giving rise to a distinguishable optical appearance. The adsorption of the receptor may also create defects in the liquid crystal. In some embodiments, the receptor species is reversibly adsorbed on the surface of the liquid crystal. For example, when an aqueous solution with a suitable concentration of SDS, for example an aqueous 1 mM SDS solution, is contacted with 5CB confined within a TEM grid or a well of a substrate, the optical appearance of the liquid crystal becomes dark indicating formation of the interfacial membrane and homeotropic alignment of the 5CB. When an aqueous solution free of SDS is subsequently contacted with the interfacial membrane, the optical appearance becomes bright again indicating desorption of the SDS from the liquid crystal. In other more preferred embodiments, the receptor species is more strongly adsorbed on the surface of the liquid crystal and forms a stable interfacial membrane. In such embodiments, desorption does not occur when the interfacial membrane formed from these receptor species is subsequently contacted with an aqueous solution free of the receptor species. Interfacial membranes formed from phospholipids such as DLPC, DPPC, DLPE, and DPPE are examples of receptor species that are strongly adsorbed on the surface of a liquid crystal confined in a grid or well of a substrate. Liquid crystal devices in which a receptor species is strongly adsorbed on the liquid crystal may be flushed with water or an aqueous solution and then contacted with an aqueous solution containing an analyte allowing interaction with the receptor and/or detection of the analyte to be examined.

In one embodiment, phospholipids such as DLPC, DPPC, DLPE, and DPPE and/or other receptor species such as those described above may be adsorbed on the surface of a liquid crystal in a well or grid of a substrate using a surfactant-mediated method. In the surfactant-mediated method an aqueous solution containing the receptor and a surfactant are contacted with the liquid crystal. Surfactant mediated delivery of receptors involves first dissolving a mixture of surfactant and receptor molecules directly into an aqueous solution containing various buffers at various pHs. Surfactant to receptor ratios typically range from 1:1 to 1000:1 with preferred ranges being from 1:1 to 50:1 and from 1:1 to 10:1. The exact surfactant to receptor ratio will depend on the relative solubilities of the two components within micelles, the shape of the surfactant, and the total concentration of the surfactant. The surfactant generally has a critical aggregation concentration that is greater than 1 nM or in some cases is greater than 1 μM, and the desired concentration of the surfactant will generally be at or above its critical micelle concentration which generally ranges from 1 nM to 100 mM or from 1 μm to 100 mM. Typical receptor concentrations range from 1 nM to 100 mM. Suitable surfactants include non-ionic surfactants, ionic surfactants, zwitterionic surfactants, polymeric surfactants, and polymers. In some embodiments, the surfactant is an anionic surfactant, a cationic surfactant, or a non-ionic surfactant. Examples of anionic surfactants include, but are not limited to, alkyl sulfates such as SDS, di-2-ethylhexyl sodium sulfosuccinate, carboxylic acids, or combinations of these. Examples of cationic surfactants include, but are not limited to, organoammonium compounds, organoferrocenium compounds, organopyridinium compounds, organoamine oxides, glucosides, or combinations of these. Examples of non-ionic surfactants include, but are not limited to, alcohols, and compounds including one or more ethylene oxide repeat units such as Tween@ or Triton@ brand non-ionic surfactants. The surfactant may include two different headgroups such as in hydroxyalkylammonium compounds, hydroxyalkylsulfates, ferrocenylalkylammonium compounds, and ferrocenylalkyl sulfates. Quaternary ammonium compounds such as CTAB and DTAB are especially useful in the surfactant-mediated method for preparing liquid crystal devices of the present invention. It is desirable that the surfactant be water soluble facilitating its removal from the interface by exchange of the aqueous phase with one free of surfactant in the bulk. Suitable surfactants also include phospholipids or other surface-active components of biological systems. Generally, the receptor should be insoluble or at least sparingly soluble in the aqueous phase. The buffer components may include phosphates, acetates, tris, HEPES, MOPS, sodium chloride, potassium chloride, calcium chloride, and EDTA in concentrations ranging from 1 μM to 1 M with a preferred concentration range being 1 mM to 100 mM. The buffers may range in pH from 2-12, from pH 4-10, or from pH 6-9. Mixtures of the surfactant and receptor molecules are allowed to adsorb at the liquid crystal-aqueous interface for time periods ranging from 5 minutes to 1200 minutes with preferred adsorption times ranging from 15 minutes to 120 minutes. The exact time is dictated by the alignment of the liquid crystal which attains a desired homeotropic alignment indicating sufficient adsorption of the surfactant and receptor. The interface may then be "cleaned" of the surfactant by subsequent exposure of the interface to an aqueous solution that does not contain the receptor or surfactant molecules for periods of time ranging from 5 minutes to 1200 minutes with preferred times ranging from 5 minutes to 60 minutes. After the phospholipid has been adsorbed on the liquid crystal, an aqueous solution free of phospholipid and surfactant may be used to remove unreacted phospholipid and surfactant from the liquid crystal device. Surprisingly and unexpectedly, interfacial membranes prepared by the surfactant-mediated method typically afford more densely packed layers than those prepared by vesicle adsorption in the absence of a separate surfactant. This method is particularly suited for preparing layers of lipids which are below their gel to liquid crystal transition temperature at the temperature of the experiment such as phospholipids with fatty acid chain lengths of more than 12 carbon atoms.

Surprisingly and unexpectedly, the surfactant mediated approach results in an aggregate of surfactant and phospholipid having higher diffusivity and fluidity than observed when phospholipid is adsorbed without a separate surfactant species. These properties allow the mass transfer of lipid to the aqueous-LC interface to occur more quickly and to greater equilibrium surface pressures. In the case of species which form vesicles in the gel state such as DPPC at room temperature, this approach allows increased equilibrium adsorption of the surfactant. The result of this approach is the creation of an interface hosting higher densities of receptor allowing for better resistance to non-specific adsorption. Additionally, this approach allows for the creation of layers of species which otherwise are insoluble as monomers or don't form vesicles in aqueous solutions (such as phosphatidyl ethanolamines).

In another method for forming a liquid crystal device with a receptor species, a suitable surface-active receptor species is first dissolved in a liquid crystal. When the liquid crystal device is placed in an aqueous solution or when an aqueous solution is passed over the top surface of the liquid crystal, the surface-active receptor species migrates to the liquid crystal-aqueous interface forming an interfacial membrane. Suitable surface-active receptor species for use with this method include any receptors that are surface-active and which are capable of being dispersed or dissolved within the liquid crystal. The liquid crystal containing the surface-active receptor species is then deposited within the holding compartments of the substrates according to any of the methods described herein such as by use of a pipette. As an example, 500 μL of hexane that contains DPPC is added to 100 μL of 5CB, and the mixture is sonicated for 30 minutes. The solution is then placed under vacuum using a vacuum pump attached to a rotary evaporator for 60 minutes to remove the excess dichloromethane. The 5CB containing the DPPC is then equilibrated for two days at room temperature. Using a gold grid supported on a hydrophobically modified glass slide (OTS-treated), the 5CB/DPPC mixture is loaded into the grids using the methods described herein. The grids are then immersed in aqueous solutions, and the DPPC migrates to the surface of the liquid crystal forming an interfacial layer at the liquid crystal-aqueous interface.

Aqueous solutions containing compounds may be contacted with a liquid crystal on which a receptor species is adsorbed to detect interactions or chemical reactions between the compound and the adsorbed receptor. In this manner, the devices of the present invention may be employed to detect interactions (binding and/or chemical reaction) of known analytes with a given receptor species or may be used to detect or identify a given analyte in an aqueous solution. Various analytes may be used in accordance with the liquid crystal devices of the present invention. Examples of analytes include proteins such as phospholipases such as $PLA_1$ and $PLA_2$, cytochrome c, BSA, and lysozyme. The role of the receptor and analyte may be reversed by changing which species is hosted within the adsorbed layer at the liquid crystal-aqueous interface. Examples of such interactions are biotin and avidin, streptavidin, and antibiotin-IgG; growth factors and growth factor receptors; hormones and hormone receptors; enzymes and enzyme inhibitors, substrates, and initiators; antibodies and antigens; integrins and components of the extracellular matrix; cell signaling proteins as part of a cascade; and ion channel proteins and ions and activating ligands. Generally, analyte concentrations in the aqueous solutions may range from 1 fM to 1 M with the desirable concentration depending on the nature of the interaction between the analyte and the receptor. Suitable buffers for aqueous solutions that include analytes include those used to prepare the interfacial membrane. For biological analytes, the pH of aqueous solutions should typically range from 6 to 9.

Figure 3:
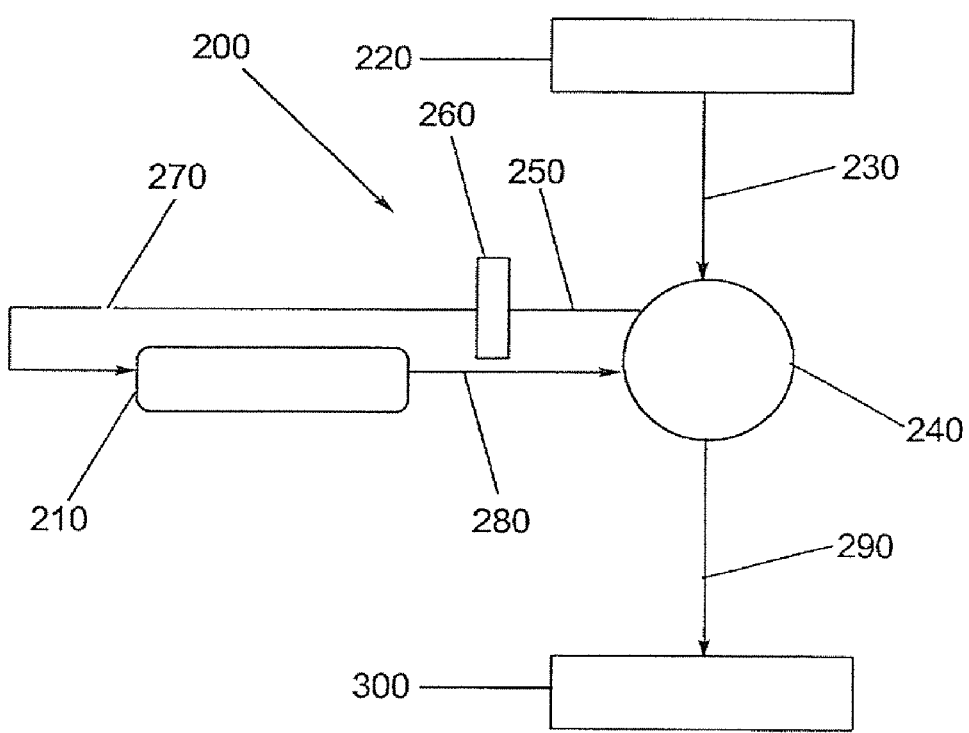
FIG. 3 is a schematic diagram of an apparatus used to circulate an aqueous solution through a liquid crystal device of the present invention.

Liquid crystal devices with receptors such as phospholipids that are strongly adsorbed to the top surface of the liquid crystal may be used in conjunction with an apparatus such as that shown in FIG. 3. FIG. 3 is a schematic diagram of an apparatus 200 that may be used to circulate an aqueous solution through a container 210 holding a liquid crystal device of the present invention. As shown in FIG. 3, a first reservoir 220 containing an aqueous solution supplies the aqueous solution through first line 230 to a peristaltic pump 240 or other pumping device. From peristaltic pump 240, the aqueous solution flows through second line 250 through an optional filter 260 and into a third line 270 which supplies the aqueous and optionally filtered solution through a first opening or inlet and into to the container 210 holding a liquid crystal device of the invention. After circulating through the container 210 holding the liquid crystal device and over the top surface of the liquid crystal, the aqueous solution exits container 210 through a second opening or outlet and into fourth line 280 and is pumped by peristaltic pump 240 into line 290 which supplies the aqueous waste to a waste reservoir 300. One of skill in the art will recognize that the aqueous waste could be circulated from container 210 holding the liquid crystal device back into the first reservoir 220 rather than waste reservoir 300 in an alternative arrangement that allows a particular aqueous solution to be continuously circulated through a liquid crystal device of the invention. This may be useful where the concentration of the analyte is very low in the aqueous solution, but the interaction between the analyte and the receptor is very strong. One skilled in the art will recognize that first reservoir 220 may be replaced with similar reservoirs containing a different aqueous solution to change the solution contacting the liquid crystal device. Thus, first reservoir 220 may initially contain an aqueous solution with a receptor such as, but not limited to, DPPC, DLPC, DLPE, or DPPE vesicles, so that the receptor is adsorbed on the surface of the liquid crystal and forms an interfacial membrane between the top surface of the liquid crystal and the water. Adsorption of a suitable amount of the receptor will be indicated by a change in the orientation of the liquid crystal. After a suitable amount of the receptor species has been adsorbed on the surface of the liquid crystal and a suitable interfacial membrane has formed, the aqueous solution in first reservoir 220 may be replaced with a buffered aqueous solution to flush the system. The flushing solution in first reservoir 220 may then be replaced with an aqueous solution containing a known analyte such as, but not limited to, BSA. PLA2, cytochrome c, lysozyme, or another protein or an unknown analyte for circulation over a liquid crystal device of the present invention. As the aqueous solution containing the analyte flows over the surface of the membrane formed on the surface of the liquid crystal, any interaction between the membrane receptor molecules and the analyte will be detected by a change in the orientation in the liquid crystal such as evidenced by a change from dark to bright caused by disruption of the homeotropic anchoring of the liquid crystal. As explained in Example 6, and shown in FIGS. 10A-10F, receptor molecules such as DPPC and DLPC adsorbed on liquid crystals may be used to examine enzymatic activity of species such as PLA2 and may also be used to distinguish between binding of enzymes to receptor molecules and reaction of analytes such as enzymes with receptor molecules.

Figure 4:
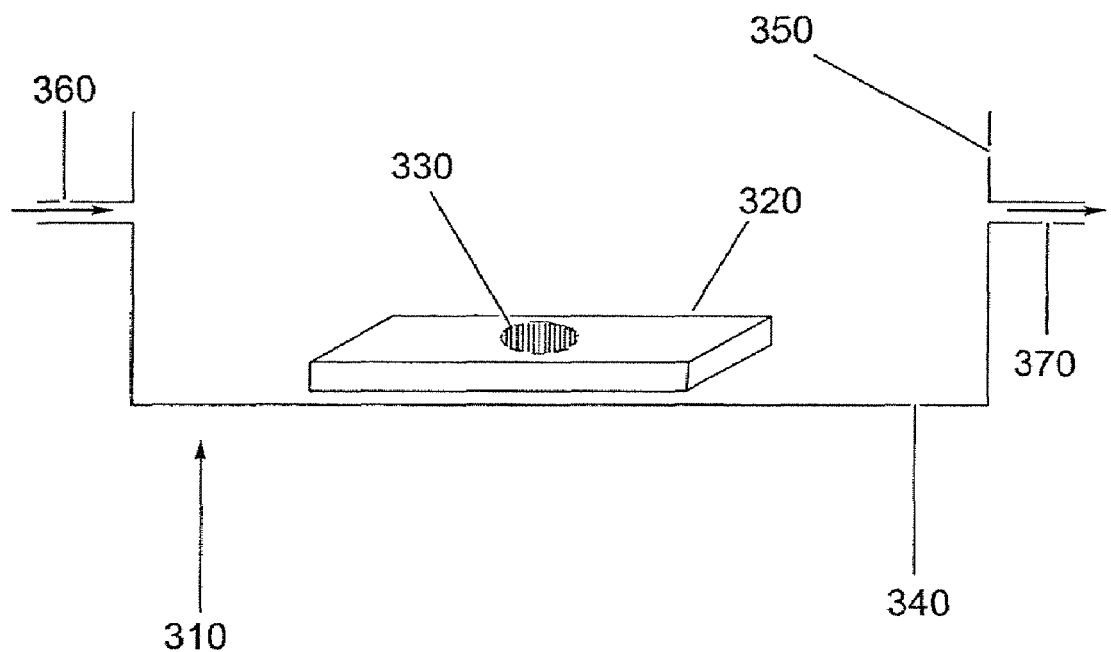
FIG. 4 is a cross-sectional side view of a liquid crystal device having a substrate disposed in a container with an inlet and an outlet.

As described above, liquid crystal devices of the present invention may include a container having an inlet and an outlet. Such devices may be used where a sample is to be flowed over the top of a liquid crystal in a holding compartment of a substrate. FIG. 4 is a cross-sectional side view of one such liquid crystal device. As shown in FIG. 4, a liquid crystal device may include a container 310 and a substrate disposed within the container. For example, the device may include a glass slide 320 on which a grid 330 is positioned that is disposed inside container 310. Container 310 is defined by bottom wall 340 and side walls 350. Side walls 350 of container 310 define an inlet 360 and an outlet 370 through which a sample may be introduced and removed from container 310. Inlet 360 and outlet 370 may be configured to project out the sides of container 310 or alternatively may simply be holes defined by side walls 350. Those skilled in the art will recognize that various other configurations are possible and may be used. Preferably, outlet 370 will be positioned at a height in container 310 such that a liquid introduced into container 310 through inlet 360 will remain over the top of a liquid crystal placed in the holding compartment of a substrate disposed in container 310.

When DLPC or DLPE interfacial membranes adsorbed on 5CB in a gold TEM grid on an OTS-treated glass slide are contacted with an aqueous solution of $PLA_2$ in the presence of $Ca_{2+}$ ions and viewed through polarized light, the appearance of the optical texture of the 5CB changes from dark (homeotropic anchoring) to bright (planar anchoring) as a function of enzyme concentration and time as shown in the following Examples. As shown qualitatively in FIGS. 11A-11F, the reaction of $PLA_2$ with the interfacial membrane formed from DLPC is substantially faster than it is with the membrane formed from DLPE. The measurement of the brightnesses may also be used to quantitatively determine kinetic information regarding the rates of reaction. Quantitative determination of kinetic parameters from the appearance of the liquid crystal may be accomplished by plotting a measure of the optical texture (such as the average brightness (grayscale or an RGB channel), standard deviation of any measure of brightness, or a Fourier transform of the image) versus time. The data may then be analyzed by fitting the data with a model of the kinetic behavior for the given interaction (e.g. a surface reaction analogue to the Michaelis-Menton equation for enzyme kinetics).

Because the devices of the present invention may be used to detect the presence of compounds in flowing streams, the devices may be used to continuously monitor the presence of a compound that interacts with the liquid crystal or a receptor adsorbed on the surface of a liquid crystal. Additionally, the devices of the present invention may be used to monitor water quality.

In one embodiment, the invention provides a method for determining a change in the oxidation state of a molecule adsorbed on a liquid crystal. In such embodiments, the molecule includes a group such as, but not limited to, a ferrocene group that may be oxidized or reduced upon contact with an oxidizing agent, a reducing agent, an applied oxidizing potential, or an applied reducing potential. In the method, a liquid crystal device immersed in an aqueous solution is contacted with an oxidizing agent, a reducing agent, an applied oxidizing potential, or an applied reducing potential. In the liquid crystal device of such methods, the molecule is adsorbed on the top surface of a liquid crystal that is located in the holding compartment of a substrate as described above. A change in the orientation of the liquid crystal upon contacting the liquid crystal device with the oxidizing agent, the reducing agent, the applied oxidizing potential, or the applied reducing potential indicates that the oxidation state of the molecule has changed. Examples of groups that may be oxidized or reduced on the receptor molecule include, but are not limited to, ferrocene, quinone, metal tri-nitriloactetic acid complexes, ferricyanide, viologens, metal porphyrins, alcohols, aldehydes, organosulfur compounds, anthracene, azobenzene, benzophenone, nitrobenzene, RU(bpy)30+, tetracyanoquinodimethane (TCNQ), tetrathiafulvalene, and other biological redox-active species such as but not limited to neurotransmitters. One group of suitable molecules with groups that may be oxidized or reduced includes (ferrocenylalkyl)trialkyl-ammonium halides such as (ferrocenylalkyl)trimethylammonium chlorides and bromides such as 11-(feuocenylundecyl)trialkylammonium bromide. The aqueous solution in which the liquid crystal device is immersed may also include surfactants such as cationic surfactants, anionic surfactants, and/or zwitterionic surfactants. Examples include ferrocenyl surfactants; alkyltrimethylammonium halides; alkyl sulfates; phospholipids such as dilaurylphosphatidyl choline, dipalmitoylphosphatidyl choline, dilaurylphosphatidyl ethanolamine, dipalmitoylphosphatidyl ethanolamine, and combinations of these; and polymeric surfactants, such as hydrophobically modified ethylhydroxyethyl cellulose (HM-EHEC). Quaternary ammonium compounds suitable for use as surfactants include, but are not limited to, CTAB and DTAB. Typically, the aqueous solution also includes a salt such as, but not limited to, $Li_2SO_4$. Other buffering agents and salts may be included in the aqueous solutions such as, but not limited to, sodium halides, potassium halides, sodium sulfate, potassium sulfate, sodium phosphate, potassium phosphate, trig, HEPES, and MOPS.

Various oxidizing agents and reducing agents may be used in accordance with the method for determining a change in the oxidation state of a molecule adsorbed on a liquid crystal. Examples of suitable oxidizing and reducing agents include, but are not limited to, hydrogen peroxide, ascorbic acid, sodium borohydride, sodium cyanoborohydride, potassium permanganate, lithium aluminum hydride, and dithiothreitol. In embodiments such as that described in the preceding paragraph, electrochemical oxidation and/or reduction may be accomplished by connecting the aqueous solution in which the liquid crystal device is immersed with a buffered aqueous solution using a salt bridge. A working and reference electrode are then placed in the aqueous solution in which the liquid crystal device is immersed. A counter electrode is placed in the buffered aqueous solution that does not contain the liquid crystal device. The oxidizing or reducing potential may be controlled with a potentiostat. Applied reducing potentials typically range from −4 V to 0 V, from −0.8 V to 0 V, or from −0.2 V to 0 V. Applied oxidizing potentials typically range from 0 V to +4 V, from +1.0 V to 0 V, and from +0.35 V to 0 V. As will be apparent to those skilled in the art, the applied reducing or oxidizing potential should correspond to the group on the receptor molecule. A change in the oxidation state of the receptor species is indicated by the change in the orientation of the liquid crystal as viewed with polarized light.

EXAMPLES

The following materials and methodologies were utilized in the examples discussed in greater detail below.

Materials

Sodium dodecyl sulfate (SDS) at 99+% purity and aluminum oxide (activated, 50-200 μm, neutral) were obtained from Sigma (St. Louis, Mo.). The SDS was initially purified by recrystallization from ethanol (Aaper Alcohol and Chemical Co., Shelbyville, Ky.). Deionization of a distilled water source was performed using a Milli-Q system (Millipore, Bedford, Mass.) to give water with a resistivity of 18.2 MΩ cm, Octadecyltrichlorosilane (OTS), methanol, methylene chloride, sulfuric acid, hydrogen peroxide (30% w/v), sodium chloride, hexane, and heptane were all obtained from Fisher Scientific (Pittsburgh, Pa.). The 5CB was purchased from EM Sciences (New York, N.Y.). Copper and Gold TEM grids with thicknesses of 18-20 μm, hole sizes of 19, 55, 115 and 292 μm, and bar widths of 6, 7, 10, and 48 μm, respectively, were obtained from Electron Microscopy Sciences (Fort Washington, Pa.). Buffer solutions were prepared using analytical grade commercially available reagents. FTMA was obtained from Dojindo Laboratories (Japan). $Li_2SO_4$, CTAB, and DTAB were obtained from Sigma (St. Louis, Mo.). DBTAB was synthesized according to the methods of Saji et al. (Saji, T.; Hoshino, K.; Yoshiyuki, I.; Masayuki, G. *J. Am. Chem. Soc.*, 113, (1991) p. 450; and Saji, T.; Hoshino, K.; Aoyagui. S. *J. Am. Chem. Soc.* 107, (1985), p. 6865.) for addition of a quaternary ammonia to a bromine terminated alkyl chain. Purity of the synthesized DBTAB was verified by nuclear magnetic resonance spectroscopy and thin layer chromatography. HTAB was synthesized according to the methods of Gallardo et al. (Gallardo, B. S.; Metcalfe, K. L.; Abbott, N. L. *Langmuir* 12, (1996) p. 4116.) and purity was verified by nuclear magnetic resonance spectroscopy and mass spectrometry. DPPC, DLPC, D-DPPC, L-DPPC, DLPE, LLPC, PLA2, BSA, cytochrome c, and lysozyme were obtained from Sigma (St. Louis, Mo.).

The orientation of 5CB was examined using plane-polarized light in transmission mode on an Olympus BX60 microscope with crossed-polarizers. The cells were placed on a rotating stage located between the polarizers. Orthoscopic examinations were performed with the source light intensity set to 50% of full illumination and the aperture set to 10% to collimate the light rays. In-plane birefringence was determined by rotating the stage by 450 and observing modulation in the intensity of transmitted light or by the presence of brush textures emanating from a defect center. Homeotropic alignments were determined by first observing no transmission of light over a 360° rotation of the stage. Insertion of a condenser below the stage and a Bertrand lens above the stage allowed conoscopic examination of the cell. An interference pattern consisting of two crossed isogyres indicated homeotropic alignment. Optical images were captured using a digital camera (Olympus@C-2040 Zoom brand CCD camera) mounted on the microscope and set to an i-stop of 2.6 and a shutter speed of 1/320 second.

Formation of OTS-Treated Glass Slides with TEM Grids Impregnated with 5CB

The following general procedure is shown schematically in FIGS. 1A-1E. Glass microscope slides used in the experiments and marked premium grade were obtained from Fisher Scientific (Los Angeles, Calif.). The glass slides were cleaned prior to use by sequentially treating with "piranha solution" (70% $H_2SO_4$/30% $H_2O_2$) and then base solution (70% KOH, 30% $H_2O_2$) using nitrogen to provide agitation (1 hour at 50° C.). "Piranha solution" should be handled with extreme caution because it reacts violently with organic materials and should not be stored in closed containers. After cleaning, the slides were rinsed thoroughly with deionized water, ethanol, and then methanol, and then the rinsed slides were dried under a stream of nitrogen. Prior to use, the clean rinsed slides were stored in an oven heated at 110° C. for at least 2 hours.

A 0.5 mM OTS solution was prepared by adding OTS to heptane that was previously dried by passage with applied pressure through an aluminum oxide column (10 cm high and 5 cm in diameter) equipped with a glass frit to prevent aluminum oxide from passing into the dried solvent. The slides were then immersed in the 0.5 mM OTS heptane solution for 30 minutes at room temperature. The OTS-treated slides were then rinsed with methylene chloride and dried under nitrogen. The quality of the OTS layer was tested by forming a sandwich of OTS-treated slides spaced by about 15 μm using Saran® brand wrap as a spacing material. The liquid crystal 5CB was then introduced between the slides, and the resulting optical texture was examined using polarized light to confirm homeotropic anchoring. Any sample not exhibiting homeotropic anchoring of liquid crystal was rejected for further use.

Copper or gold TEM grids were cleaned sequentially in methylene chloride, ethanol, and methanol. The clean slides were then dried under nitrogen and heated in an oven at 110° C. for at least 24 hours prior to use. One or more of the grids was then placed onto the surface of an OTS-treated glass slide. Approximately 1 μL of 5CB was dispensed into each grid and the excess liquid crystal was removed by contacting a 25 μL capillary tube obtained from the Fisher Scientific (Los Angeles, Calif.) with the 5CB on the grid. This procedure led to the formation of a stable film of 5CB within the grid (did not leave the grid). The surface of the 5CB, when in contact with the aqueous phase, was approximately flat as determined by concurrent focus of the grid and 5CB under an optical microscope at objective powers ranging from 4× to 50×.

The 5CB impregnated TEM grid supported on a solid surface was quickly (typically less than 5 seconds) immersed in and withdrawn from deionized water to promote further removal of excess 5CB. These steps resulted in consistent filling of the grids prior to exposure of the grid to various solution conditions, although similar results were observed for cells prepared by removal of excess 5CB using only a capillary tube as described above. Typically, the optical cell was heated to about 50° C. and was then immediately immersed in the aqueous solution of interest held at 20° C. In other cases, the aqueous solution of interest was circulated through a device such as that shown in FIG. IE over the top of the TEM grid to form an adsorbed layer of receptor species on the top surface of the liquid crystal confined in the TEM grid.

Formation of Substrate with Wells Impregnated with 5CB

Substrates with microtextured surfaces containing wells or troughs for holding liquid crystal such as that shown in FIG. 2 are formed using the following procedure. Glass slides or silicon wafers cleaned using the procedure detailed above are coated 1 μm to 200 μm with a photoresist. By masking the photoresist, UV light may be used to etch depressions of from 1 μm to 200 μm depth having highly customizable lateral dimensions (e.g. 2 μm to 1 cm or 20 μm to 1 cm) and shapes (circles, squares, rectangles, octagons). Glass slides are then optionally subsequently treated to make the surface hydrophobic (e.g. by exposure to OTS). The patterned glass slides and silicon wafers are further used as a master to replicate the pattern into various polymeric materials such as polydimethylsiloxane, epoxy, polyethylene, polypropylene, polyurethane, and polystyrene. Replication of the master results in the formation of a negative of the pattern which may require a second replication of the resulting polymeric replica to obtain the pattern used for the master. The liquid crystal is then placed in the depressions of the substrate either by micropipeting or evaporation of the liquid crystal from a volatile solvent which is pipetted into the depressions.

Approximately 1 μL of 5CB is dispensed into the depressions in the patterned surface of the microtextured substrate and the excess liquid crystal is removed by contacting a 25 μL capillary tube obtained from Fisher Scientific (Los Angeles, Calif.) with the 5CB. This procedure leads to the formation of stable films of 5CB within the wells (did not leave the wells). The surface of the 5CB, when in contact with the aqueous phase, is approximately flat as determined by concurrent focus of the well and 5CB under an optical microscope at objective powers ranging from 4× to 50×.

The 5CB impregnated wells of the substrate is quickly (typically less than 5 seconds) immersed in and withdrawn from deionized water to promote further removal of excess 5CB. These steps result in consistent filling of the wells in the substrate with the microtextured surface prior to exposure of the substrate to various solution conditions, although similar results are observed for cells prepared by removal of excess 5CB using only a capillary tube as described above.

Typically, the optical cell is heated to about 50° C. and is then immediately immersed in the aqueous solution of interest held at 20° C. In other cases, the aqueous solution of interest is circulated through a container holding the substrate with the liquid crystal-impregnated wells over the top of the top surface of the substrate to form an adsorbed layer of receptor species on the top surface of the liquid crystal confined in the wells of the microtextured substrate.

Formation of DPPC, DLPC, and DLPE Vesicle Solutions

DPPC, DLPC, and DLPE were all procured from Sigma (St. Louis, Mo.) and used as obtained. The lipids were dissolved in chloroform (Sigma), dried under nitrogen, and placed under vacuum for 1-2 hours. The lipid was then reconstituted in a Tris-buffered solution at a pH of 8.9 to provide a total lipid concentration ranging from 0.1 mM to 1 mM. The Tris-buffered solution was then sonicated (Sonic Dismembrator 80, Fisher Scientific) for 3 pulses of 5 minutes each at a power of 15 W. This procedure provided vesicle solutions of lipid which were filtered using a 0.22 µm Millex filter (Millipore).

Example 1

Formation of Stable DLPC Adsorbed Membrane on 5CB at Various Concentrations 5CB was confined to copper TEM grids (hole size of 292 µm and thickness of 18-20 µm) placed on OTS-treated glass slides by contacting a 1 µL droplet of 5CB with the grid. Excess 5CB was removed by contacting a 25 µL capillary tube with the 5CB. The resulting film of 5CB confined to the grid was quickly immersed in and withdrawn from deionized water. The 5CB impregnated grid on the OTS-treated glass slide was then immersed in vesicle solutions of DLPC at various concentrations in 10 mM phosphate, 100 mM sodium chloride buffer at pH 8.9. In cases where the alignment of the 5CB after exposure to DLPC resulted in homeotropic anchoring of 5CB, the DLPC solution was exchanged with a pure buffer not containing DLPC while keeping the 5CB constantly immersed in the aqueous phase. The optical appearance of the 5CB was monitored using a light microscope with crossed polarizers. All images shown were taken at a magnification of 4× with an incident light aperture of 10% and relative light source intensity of 50%.

Figure 5A:
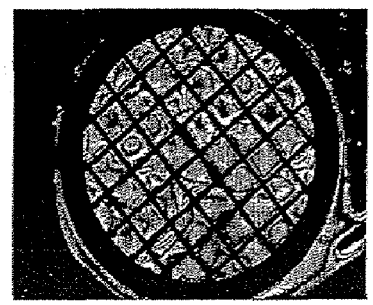
FIGS. 5A-5E are scanned images through an optical microscope with cross-polarizers of the optical texture of 5CB confined to a copper grid with grid spacings of 292 µm and a grid thickness of 18-20 µm after exposure to aqueous solutions containing DLPC vesicles at a pH of 7 buffered with 0.1 M phosphate for different lengths of time (FIG. 5A, 1 µM DLPC for 5 minutes.
Figure 5B:
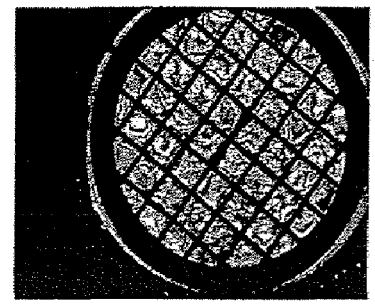
Figure 5C:
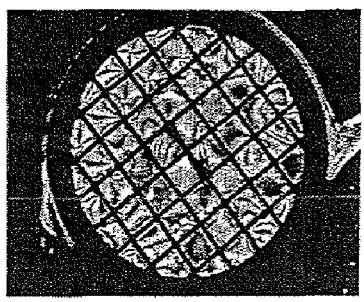
Figure 5D:
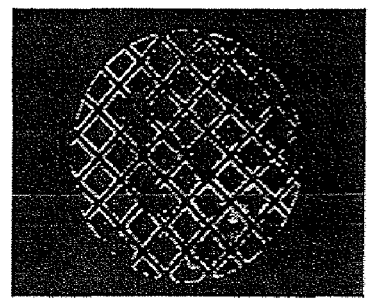
Figure 5E:
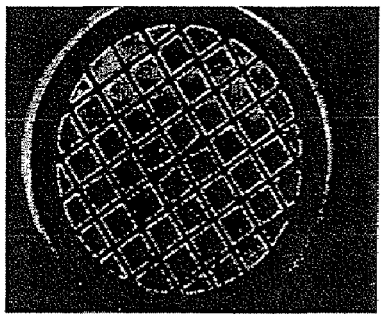
Figure 5F:
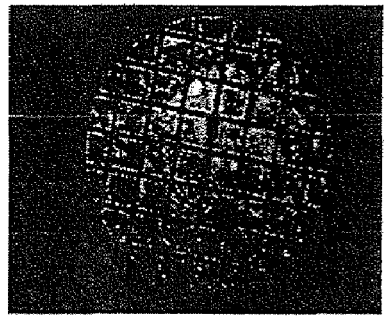
FIG. 5F is a scanned image of the optical texture of 5CB confined to a copper grid after exposure to a pH 7 buffered aqueous solution containing 10 µM DLPC for 2 hours after flushing with a pH 7 buffered aqueous solution free of DLPC for 14 hours.

As shown in FIGS. 5A 5E, formation of a DLPC layer adsorbed on the top surface of 5CB confined within a copper grid occurred more rapidly as the concentration of the phospholipid vesicles in the aqueous solution increased. The orientation of the liquid crystal changed from planar (bright appearance) to homeotropic (dark appearance) as the DLPC membrane formed at the liquid crystal/aqueous interface. As shown in FIGS. 5A and 5B, no significant adsorption of DLPC occurred on the 5CB when an aqueous solution with a concentration of 1 µM DLPC was contacted with the 5CB confined in the grids for periods up to 2 hours. As shown in FIG. 5C, no significant adsorption of DLPC occurred on the 5CB when an aqueous solution with a concentration of 10 µM DLPC was contacted with the 5CB confined in the grids for periods up to 5 minutes. However, as shown in FIG. 5D, DLPC membrane formation was clearly evident at the liquid crystal/aqueous interface when an aqueous solution with a concentration of 10 µM DLPC was contacted with the 5CB confined in the grids for periods of 2 hours. As shown in FIG. 5C, DLPC membrane formation was evident when an aqueous solution with a concentration of 10 µM DLPC was contacted with the 5CB confined in the grids for as little as 5 minutes. Formation of the adsorbed DLPC interfacial membrane was determined to be stable and irreversible. For example, as shown in FIG. 5F, when a membrane formed by exposing the 5CB to an aqueous solutions with a concentration of 10 µM DLPC was flushed for 14 hours with an aqueous solution at pH 7, the optical texture still appeared dark and unchanged indicating that the liquid crystal was still homeotropic and that the adsorbed DLPC was still present. The stability of the DLPC layer indicates that the DLPC adsorbed biomimetic membrane on the liquid crystal may be used in a circulating flow system such as that shown in FIG. 3 using a liquid crystal device such as that shown in FIG. 4.

Example 2

Interaction of Cytochrome c with DLPC Adsorbed on 5CB

5CB was confined to copper TEM grids (hole size of 292 µm and thickness of 18-20 µm) placed on an OTS-treated glass slide by contacting a 1 µL droplet of 5CB with the grid. Excess 5CB was removed by contacting a 25 µL capillary tube with the 5CB. The resulting film of 5CB confined to the grid was quickly immersed in and withdrawn from deionized water. The 5CB impregnated grid on the OTS-treated glass slide was then immersed in a 0.1 mM vesicle solution of DLPC in 10 mM phosphate, 100 mM sodium chloride buffer at a pH of 8.9. After a layer of DLPC was adsorbed between the 5CB and aqueous phase, indicated by the transition of the alignment of 5CB to a homeotropic alignment, the aqueous solution was exchanged with a 10 mM phosphate, 100 mM sodium chloride buffer at pH 8.9 which contained no DLPC. During this exchange, the DLPC-laden 5CB interface remained continuously immersed in the aqueous phase. Cytochrome c was then injected into the aqueous phase to give a concentration of 9.8 µM. The optical appearance of the 5CB was monitored using a light microscope with crossed polarizers. All images shown were taken at a magnification of 4× with an incident light aperture of 10% and relative light source intensity of 50%.

Figure 6A:
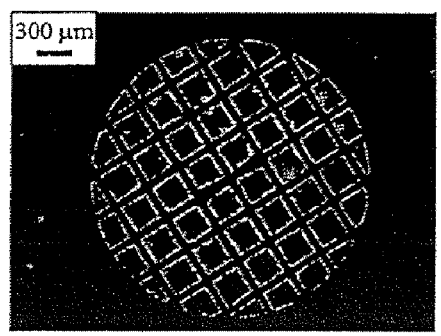
FIGS. 6A-6C are scanned images through an optical microscope with cross-polarizers of the optical texture of 5CB confined to a copper grid after exposure to an aqueous solution containing DLPC vesicles (FIG. 6A) and then after further exposure to an aqueous solution (pH of 8.9, 0.1 M phosphate buffer) containing 9.8 µM cytochrome c for 10 minutes (FIG. 6B) and 60 minutes (FIG. 6C).
Figure 6B:
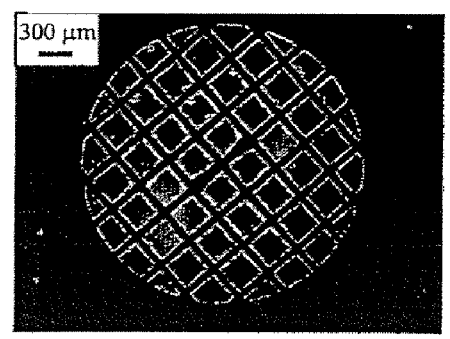
Figure 6C:
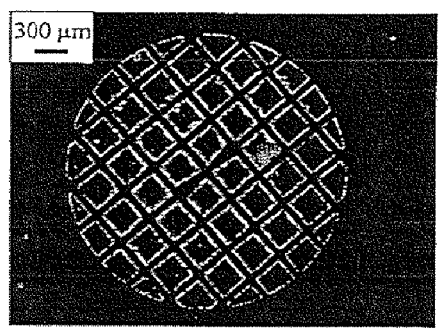

As shown in FIGS. 6A-6C, an aqueous solution containing cytochrome c at a concentration of 9.8~M does not provide any detectable interaction at the liquid crystal/aqueous interface. Thus, no brightening in the optical texture is observed even after the 5CB with adsorbed DLPC has been contacted with the 9.8 µM cytochrome c aqueous solution for a period of 60 minutes (FIG. 6C).

Example 3

Interaction of BSA with DLPC Adsorbed on 5CB

Figure 7A:
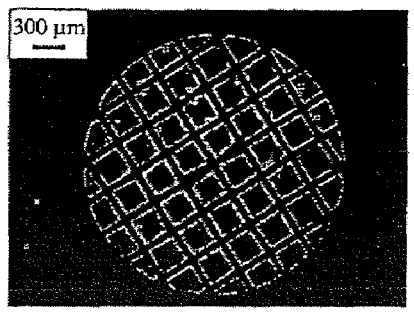
FIGS. 7A-7D are scanned images through an optical microscope with cross-polarizers of the optical texture of 5CB confined to a copper grid after exposure to an aqueous solution containing DLPC vesicles (FIG. 7A) and then after further exposure to an aqueous solution (pH of 8.9, 0.1 M phosphate buffer) containing 1.32~M BSA for 10 minutes (FIG. 7B and FIG. 7C) and 60 minutes (FIG. 7D).
Figure 7B:
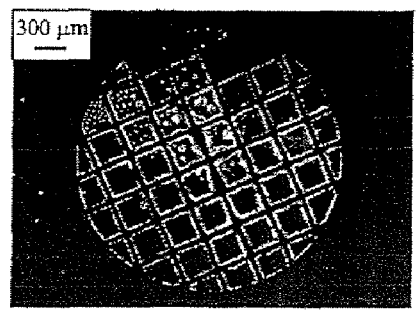
Figure 7C:
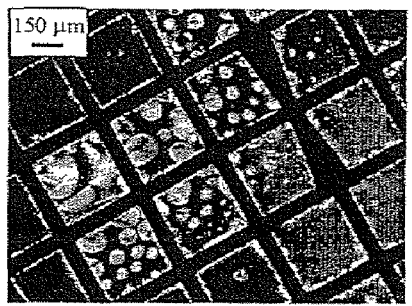

5CB was confined to copper TEM grids (hole size of 292 µm and thickness of 18-20 µm) placed on OTS-treated glass slides by contacting a 1 µL droplet of 5CB with the grid. Excess 5CB was removed by contacting a 25 µL capillary tube with the 5CB. The resulting film of 5CB confined to the grid was quickly immersed in and withdrawn from DI water. The 5CB impregnated grid on the OTS-treated glass slide was then immersed in a 0.1 mM vesicle solution of DLPC in 10 mM phosphate, 100 mM sodium chloride buffer at a pH of 8.9. After a layer of DLPC was adsorbed between the 5CB and aqueous phase, indicated by the transition of the alignment of 5CB to a homeotropic alignment, the aqueous solution was exchanged with a 10 mM phosphate, 100 mM sodium chloride buffer at pH 8.9 which contained no DLPC. During this exchange, the DLPC-laden 5CB interface remained continuously immersed in the aqueous phase. Bovine serum albumin was then injected into the aqueous phase to give a concentration of 1.32 µM. The optical appearance of the 5CB was monitored using a light microscope with crossed polarizers. All images shown were taken at a magnification of 4× (except FIG. 7C where a magnification of 10× was used) with an incident light aperture of 10% and relative light source intensity of 50%.

Figure 7D:
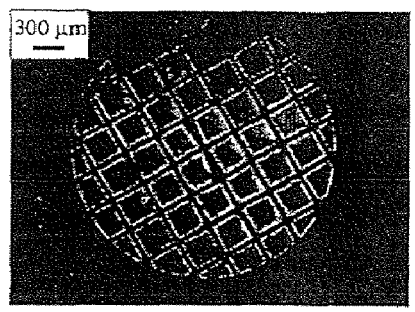

As shown in FIGS. 7A-7D, when an aqueous solution containing BSA at a concentration of 1.32 µM was contacted with the device including the DLPC adsorbed membrane on the 5CB, a transient formation of domains was observed (See FIGS. 7B and 7C) after a 10 minute exposure time. However upon continued contact with the aqueous BSA solution, the domains disappeared. Thus, as shown in FIG. 7D, no domains were visible in the optical texture after 60 minutes of contact with the 1.32 µM BSA solution. The appearance of transient domains in the alignment of the liquid crystal is significant for two reasons. First, the existence of discrete domains of 5CB alignment indicates the ability to image the lateral organization of adsorbed layers. Second, the transient nature of the domains indicates the discrimination of the alignment of 5CB of different natures of interactions with the adsorbed layer. In the case of non-specific adsorption (i.e. BSA), the domains are transient whereas in the case of specific adsorption (i.e. $PLA_2$) the domains are persistent for the lifetime of the experiment.

Example 4

Interaction of PLA2 and BSA with CTAB Adsorbed on 5CB

5CB was confined to copper TEM grids (hole size of 292~m and thickness of 18-20 µm) placed on OTS-treated glass slides by contacting a 1 µL droplet of 5CB with the grid. Excess 5CB was removed by contacting a 25 µL capillary tube with the 5CB. The resulting film of 5CB confined to the grid was quickly immersed in and withdrawn from deionized water. The 5CB impregnated grid on the OTS-treated glass slide was then immersed in a 0.1 mM CT AB in 10 mM phosphate, 100 mM sodium chloride aqueous buffer solution at a pH of 8.9. After a layer of CT AB was adsorbed between the 5CB and aqueous phase, indicated by the transition of the alignment of 5CB to a homeotropic alignment, BSA or $PLA_2$ was then injected into the aqueous phase to give a concentration of 1.32 µM. The optical appearance of the 5CB was monitored using a light microscope with crossed polarizers. All images shown were taken at a magnification of 4× with an incident light aperture of 10% and relative light source intensity of 50%.

Figure 8A:
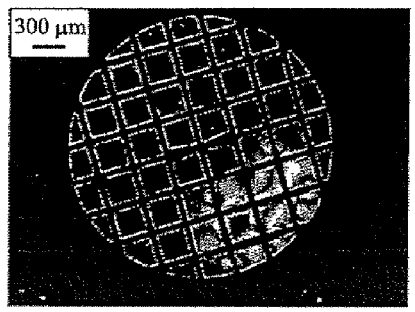
FIGS. 8A-8C are scanned images through an optical microscope with cross-polarizers of the optical texture of 5CB confined to a copper grid after exposure to an aqueous 0.1 mM solution of CTAB (FIG. 8A, pH of 8.9, 0.1 M phosphate buffer) and then after 60 minutes exposure to an aqueous solution containing 1.32 µM PLA$_2$ (FIG. 8B) or 1.32 µM BSA (FIG. 8C).
Figure 8B:
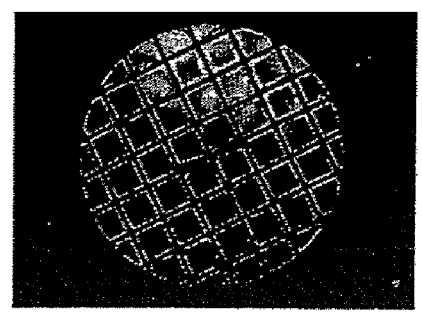
Figure 8C:
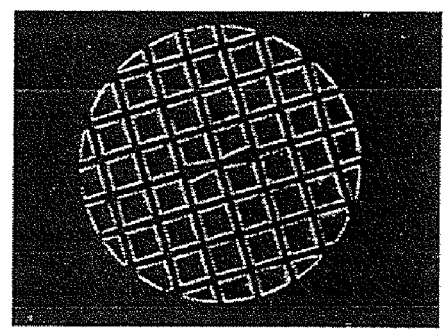

As shown in FIG. 8A, when an aqueous solution containing 0.1 mM CTAB was contacted with 5CB confined in a TEM grid, the CTAB was adsorbed on the surface of the liquid crystal. This was evidenced by a change in the optical texture from bright to dark (FIG. 8A) indicating a change in the orientation of the 5CB from planar to homeotropic. As shown in FIGS. 8B and 8C, no change in the optical texture occurred when the liquid crystal with CT AB adsorbed on the surface was contacted with aqueous solutions containing 1.32 µL $PLA_2$ (FIG. 8B) and 1.32 µm BSA (FIG. 8C) for as long as 60 minutes. This indicates that there is no interaction of $PLA_2$ or BSA with the CTAB.

Example 5

Interactions of PLA2, BSA, Cytochrome c, and Lysozyme with DLPC Adsorbed on SCB and the Role of Ca2+ on PLA2 Interaction 5CB was confined to gold TEM grids (hole size of 292 µm and thickness of 18-20 µm) placed on OTS-treated glass slides by contacting a 1 µL droplet of 5CB with the grid. Excess 5CB was removed by contacting a 25 µL capillary tube with the 5CB. The resulting film of 5CB confined to the grid was quickly immersed in and withdrawn from deionized water. The 5CB impregnated grid on the OTS-treated glass slide was then immersed in a 0.1 mM vesicle solution of DLPC in Tris-buffer at a pH of 8.9. After a layer of DLPC was adsorbed between the 5CB and aqueous phase, indicated by the transition of the alignment of 5CB to a homeotropic alignment, the aqueous solution was exchanged with Tris-buffer containing either 5 mM $CaCl_2$ or 5 mM EDTA at pH 8.9 which contained no DLPC. During this exchange, the DLPC-laden 5CB interface remained continuously immersed in the aqueous phase. The proteins were then injected to give the total concentration indicated. The optical appearance of the 5CB was monitored using a light microscope with crossed polarizers. All images shown were taken at a magnification of 4× with an incident light aperture of 10% and relative light source intensity of 50%.

Figure 9A:
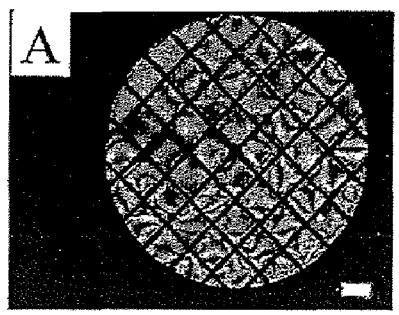
FIGS. 9A-9F are scanned images through an optical microscope with cross-polarizers of the optical texture of 5CB confined to a gold TEM grid after exposure to aqueous solutions containing DLPC vesicles for 2 hours and then after a 90 minute exposure to a 1 nM PLA$_2$, Tris-buffered 5 mM CaCl$_2$ aqueous solution (FIG. 9A); a Tris-buffered 5 mM CaCl$_2$ aqueous solution (FIG. 9B); a 1 µM PLA$_2$, 5 mM EDTA, Tris-buffered aqueous solution (FIG. 9C); a 1 µM BSA, Tris-buffered 5 mM CaCl$_2$ aqueous solution (FIG. 9D); a 10 µM cytochrome c, Tris-buffered 5 mM CaCl$_2$ aqueous solution (FIG. 9E); or a 1 µM lysozyme, Tris-buffered 5 mM CaCl$_2$ aqueous solution (FIG. 9F).
Figure 9B:
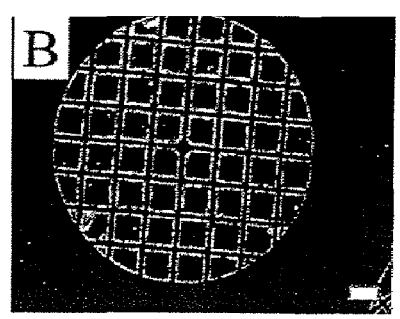
Figure 9C:
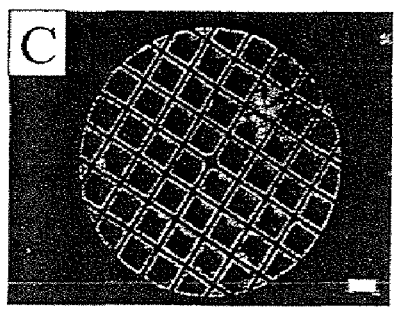
Figure 9D:
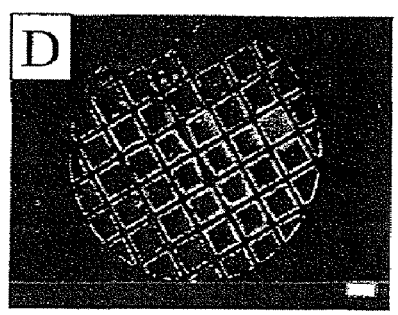
Figure 9E:
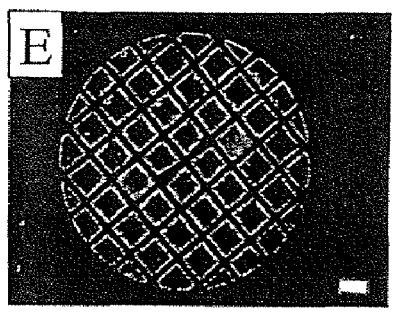
Figure 9F:
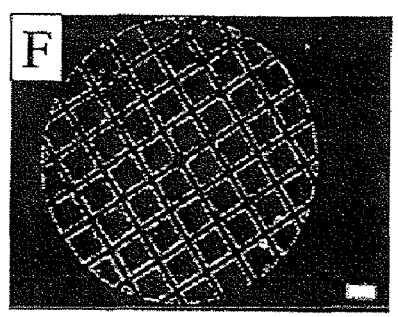

When a DLPC interfacial membrane adsorbed on the top surface of 5CB confined within a gold grid was contacted with a 1 nM PLA2 Tris-buffered 5 mM $CaCl_2$ aqueous solution, the optical appearance changed from dark to bright (FIG. 9A) and typically reached completion after 90 minutes indicating binding or reaction of the PLA2 with the DLPC. In direct contrast, in a control experiment where a Tris-buffered 5 mM $CaCl_2$ aqueous solution without $PLA_2$ was contacted with the DLPC adsorbed on the surface of the 5CB, no change in the optical appearance was observed after more than 6 hours had elapsed (FIG. 9B). As shown in FIG. 9C, when a 1 µM $PLA_2$ 5 mM EDTA Tris-buffered aqueous solution was contacted with the DLPC adsorbed on the 5CB, no change in optical appearance was observed after more than 6 hours had elapsed. This result indicated that in the absence of $Ca^{2+}$, the $PLA_2$ does not bind or react with the DLPC. As shown in FIG. 9D, no change in optical appearance occurred when a 1 µM BSA in Tris-buffered 5 mM $CaCl_2$ aqueous solution was contacted with the DLPC interfacial membrane on the 5CB for more than 12 hours. As similarly shown in FIG. 9E, no change in optical appearance occurred when a 10 µM cytochrome c in Tris-buffered 5 mM $CaCl_2$ aqueous solution was contacted with the DLPC interfacial membrane on the 5CB for more than 12 hours. Finally, as shown in FIG. 9F, no change in optical appearance occurred when a 1 µM lysozyme in Tris-buffered 5 mM $CaCl_2$ aqueous solution was contacted with the DLPC interfacial membrane on the 5CB for more than 12 hours. Collectively, these results show that $Ca^{2+}$ ions are necessary for PLA2 interaction with the DLPC interfacial membrane on the 5CB and that the DLPC interfacial membrane adsorbed on the 5CB is selective and does not interact with other proteins.

Example 6

Interaction of PLA2 with D-DPPC and L-DPPC Adsorbed on SCB Using DTAB and the Role of Ca2+ Ions on PLA2 Interaction CB was confined to gold TEM grids (hole size of 292 µm and thickness of 18-20 µL) placed on OTS-treated glass slides by contacting a 1 µL droplet of 5CB with the grid. Excess 5CB was removed by contacting a 25 µL capillary tube with the 5CB. The resulting film of 5CB confined to the grid was quickly immersed in and withdrawn from deionized water. The 5CB impregnated grid on the OTS-treated glass slide was then immersed in a 3 mM DT AB and 0.1 mM D-DPPC or L-DPPC (obtained from Sigma) micellar solution in Tris-buffer at a pH of 8.9. After a layer of DTAB and DPPC was adsorbed between the 5CB and aqueous phase, indicated by the transition of the alignment of 5CB to a homeotropic alignment, the aqueous solution was exchanged with Tris-buffer containing either 5 M $CaCl_2$ or 5 mM EDT A at pH 8.9 which contained no DTAB or DPPC. During this exchange, the 5CB interface remained continuously immersed in the aqueous phase. $PLA_2$ was then injected at the concentrations indicated. The optical appearance of the 5CB was monitored using a light microscope with crossed polarizers. All images shown were taken at a magnification of 4× with an incident light aperture of 10% and relative light source intensity of 50%.

Figure 10A:
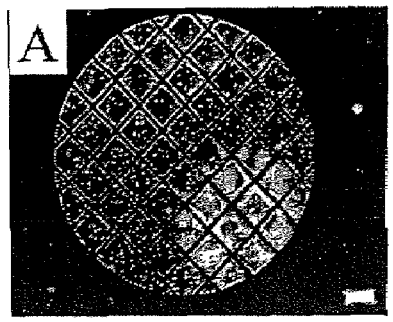
FIGS. 10A-10F are scanned images through an optical microscope with cross-polarizers of the optical texture of 5CB confined to a gold TEM grid after exposure to 3 mM DTAB, Tris-buffered aqueous solutions containing either 0.1 mM L-DPPC vesicles (FIGS. 10A-10C) or 0.1 mM $_D$-DPPC vesicles (FIGS. 10D-10F) and then flushing with Tris-buffered aqueous solutions.
Figure 10D:
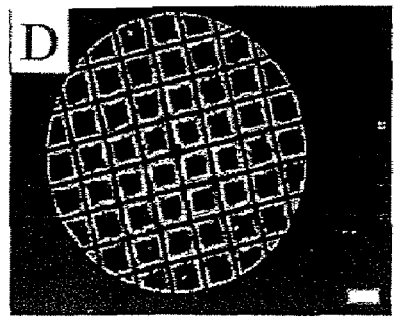
Figure 10B:
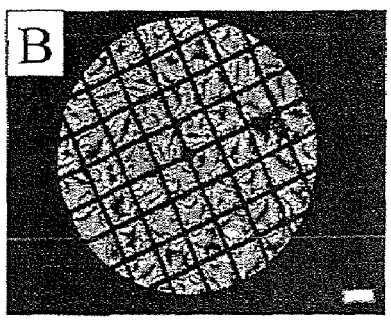
Figure 10E:
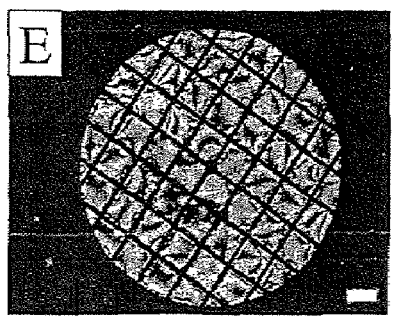
Figure 10C:
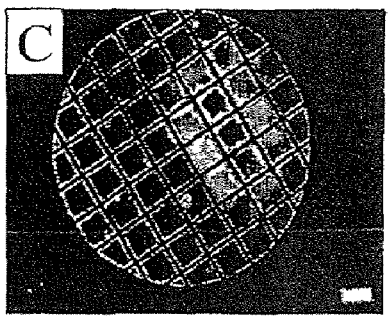
Figure 10F:
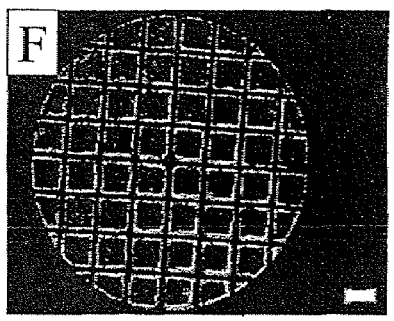

When an L-DPPC interfacial membrane adsorbed on the top surface of 5CB confined within a gold grid and formed in the presence of DTAB was contacted with a 1 nM $PLA_2$ Tris-buffered 5 mM $CaCl_2$ aqueous solution, the optical appearance of the liquid crystal changed such that small bright spots appeared (FIG. 10A). In direct contrast, when a D-DPPC interfacial membrane adsorbed on the top surface of 5CB confined within a gold grid and formed in the presence of DT AB was contacted with a 1 nM PLA2 Tris-buffered 5 mM $CaCl_2$ aqueous solution. no change in the optical appearance was observed (FIG. 10D). A comparison of these results indicates that $PLA_2$ is enantiospecific and catalyzes the formation of LPPC when L-DPPC vesicles are used to create the membrane at the liquid crystal/aqueous interface, but does not do so when D-DPPC vesicles are used. As shown in FIG. 10B, when a 100 nM $PLA_2$ 5 mM $CaCl_2$ Tris-buffered aqueous solution was contacted with L-DPPC adsorbed on the 5CB, the optical texture became bright indicating a change in orientation of the liquid crystal. The same result was obtained when a 100 nM $PLA_2$ 5 mM $CaCl_2$ Tris-buffered aqueous solution was contacted with D-DPPC adsorbed on the 5CB (FIG. 10E). Collectively, these results indicate that in the presence of $Ca^{2+}$ ions PLA2 binds to both L-DPPC and D-DPPC membranes on 5CB (FIGS. 10B and 10E), but reacts with L-DPPC and not D-DPPC (FIGS. 10A and 10D). As shown in FIGS. 10C and 10F, no change in the appearance of the optical texture was observed when L-DPPC or D-DPPC adsorbed on 5CB was contacted with 100 nM $PLA_2$ 5 mM EDTA Tris-buffered aqueous solutions. When compared to the above results, these results indicate that in the absence of $Ca^{2+}$ ions, $PLA_2$ does not interact with L-DPPC or D-DPPC adsorbed on 5CB at these concentrations. Finally, the results show that the threshold for detecting binding events may be higher than the threshold for detecting enzymatic reactions. This is consistent with the concentration levels generally used in protein binding versus enzyme kinetics studies. The results also show that phospholipid membranes formed in the presence of a surfactant such as DTAB can show improved sensitivity and performance characteristics.

Example 7

Interaction of $PLA_2$ with Interfacial Biomimetic Membranes Formed from DLPC and DLPE Vesicles CB was confined to gold TEM grids (hole size of 292 μm and thickness of 18-20 μm) placed on OTS-treated glass slides by contacting a 1 μL L droplet of 5CB with the grid. Excess 5CB was removed by contacting a 25 μL capillary tube with the 5CB. The resulting film of 5CB confined to the grid was quickly immersed in and withdrawn from deionized water. The 5CB impregnated grid on the OTS-treated glass slide was then immersed in a 0.1 mM vesicle solution of DLPC or DLPE in Tris-buffer at a pH of 8.9. After a layer of DLPC or DLPE was adsorbed between the 5CB and aqueous phase, indicated by the transition of the alignment of 5CB to a homeotropic alignment, the grids were withdrawn from the vesicle solution and placed into a Tris-buffer containing 5 mM $CaCl_2$ at pH 8.9 which contained no DLPC or DLPE. Using this method, the DLPC-laden 5CB interfaces and the DLPE-laden 5CB interfaces were allowed to coexist in the same aqueous solution. PLA2 was then injected to give a concentration of 1 nM. The optical appearance of the 5CB was monitored using a light microscope with crossed polarizers. All images shown were taken at a magnification of 4× with an incident light aperture of 10% and relative light source intensity of 50%.

Figure 11A:
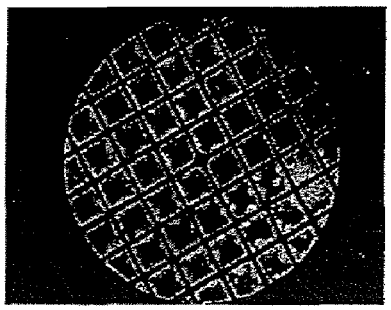
FIGS. 11A-11F are scanned images through an optical microscope with cross-polarizers of the optical texture of 5CB confined to a gold TEM grid after exposure to aqueous vesicle solutions of DLPC (FIGS. 11A-11C) or DLPE (FIGS. 11D-11F) for 8 hours and then contacting with 1 nM PLA$_2$, Tris-buffered 5 mM CaCl$_2$ aqueous solutions for various time lengths (0 minutes (FIGS. 11A and 11D); 90 minutes (FIGS. 11B and 11E); and 180 minutes (FIGS. 11C and 11F).
Figure 11D:
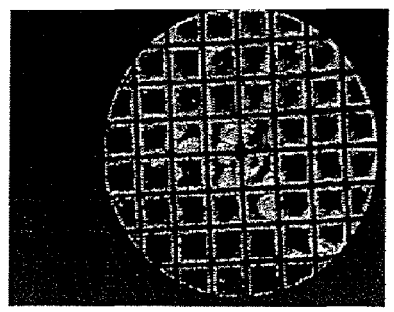
Figure 11B:
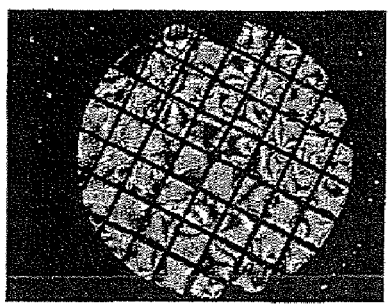
Figure 11E:
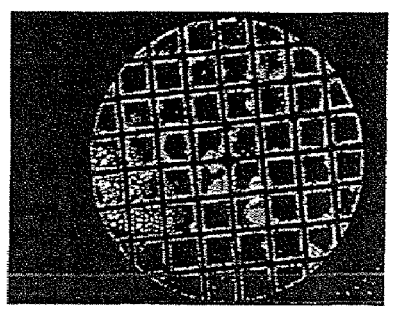
Figure 11C:
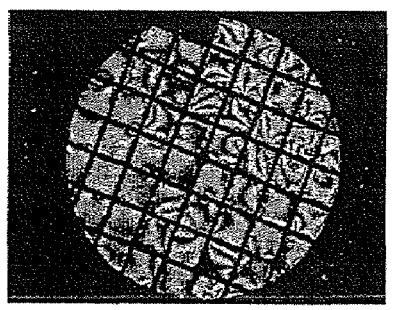
Figure 11F:
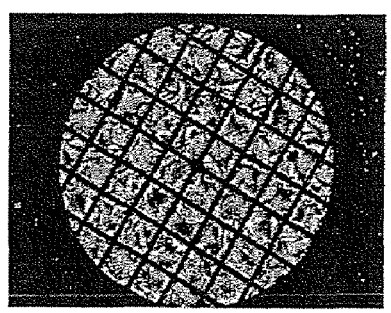

The reaction of interfacial membranes formed from DLPC and DLPE vesicles with $PLA_2$ in the presence of $Ca^{2+}$ ions were compared. As shown in FIG. 11A, the optical appearance of the 5CB with DLPC adsorbed on the surface appeared dark indicating homeotropic anchoring of the liquid crystal. The optical appearance of the 5CB with DLPE adsorbed on the surface appeared similarly dark indicating homeotropic anchoring of the liquid crystal (FIG. 11D). After 90 minutes of contact with a 1 nM $PLA_2$ Tris-buffered 5 mM $CaCl_2$ aqueous solution, the DLPC interfacial membrane appeared bright indicating significant binding of the enzyme (FIG. 11B) whereas the DLPE membrane exhibited only a slight change in appearance (FIG. 11E). After 180 minutes of contact with the 1 nM $PLA_2$ Tris-buffered 5 mM $CaCl_2$ aqueous solution, the DLPC interfacial membrane continued to appear bright indicating significant binding of the enzyme (FIG. 11C). After 180 minutes of contact with the 1 nM PLA2 Tris-buffered 5 mM $CaCl_2$ aqueous solution, the DLPE interfacial membrane also appeared bright (FIG. 11F) and similar to the appearance of the device formed using DLPC vesicles after contact with the $PLA_2$ solution for 90 minutes (FIG. 11B). These results show that $PLA_2$ interacts with the DLPC at a faster rate than it does with the DLPE. Furthermore, the above results demonstrate that the devices of the present invention may be used to both qualitatively and quantitatively compare rates of reaction with various analytes or for a given analyte and different species adsorbed to the liquid crystal. Rate of reaction information may be obtained by plotting the optical brightness of a device as a function of exposure time. The brightness of the liquid crystal is recorded using a CCD camera. NIH Image brand software is used to calculate the brightness of the liquid crystal. The brightness is plotted as a function of time to obtain the characteristic rate of reaction. Other measures of the optics that may also be used include the standard deviation of the brightness, specific color channel intensities, and Fourier transforms of the images.

Example 8

Interaction of SCB with Lauric Acid and LLPC

5CB was confined to gold TEM grids (hole size of 292 μm and thickness of 18-20 μm) placed on OTS-treated glass slides by contacting a 1 μL droplet of 5CB with the grid. Excess 5CB was removed by contacting a 25 μL capillary tube with the 5CB. The resulting film of 5CB confined to the grid was quickly immersed in and withdrawn from deionized water. The 5CB impregnated grid on the OTS-treated glass slide was then immersed in solutions of 0.1 mM lauric acid (Sigma, St. Louis, Mo.), 0.1 mM LLPC (Sigma, St. Louis, Mo.), or 0.1 mM lauric acid and 0.1 mM LLPC. The buffer in all the experiments was 10 mM phosphate and 10 mM sodium chloride at a pH of 8.9. After allowing the lauric acid and/or LLPC to adsorb at the 5CB-aqueous interface, indicated by the presence of homeotropic anchoring of 5CB for solutions containing LLPC or 2 hours for the lauric acid solution which did not change the alignment of 5CB at this concentration, the aqueous phase was exchanged for a 10 mM phosphate, 100 mM sodium chloride solution at pH 8.9 which contained neither lauric acid nor LLPC. During this exchange, the DLPC-laden 5CB interface remained continuously immersed in the aqueous phase. The optical appearance of the 5CB was monitored using a light microscope with crossed polarizers. All images shown were taken at a magnification of 4× with an incident light aperture of 10% and relative light source intensity of 50%.

Figure 12A:
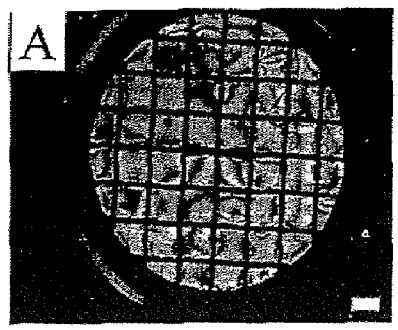
FIGS. 12A-12F are scanned images through an optical microscope with cross-polarizers of the optical texture of 5CB confined to a gold TEM grid after 1 hour contact with 0.1 mM lauric acid aqueous solution (FIG. 12A) and then flushing with a pH 8.9, 0.1 M phosphate buffer solution for 15 minutes (FIG. 12B); after 1 hour contact with 0.1 mM LLPC aqueous solution (FIG. 12C) and then flushing with pH 8.9, 0.1 M phosphate buffer solution for 15 minutes (FIG. 12D); or after 1 hour contact with 0.1 mM lauric acid and 0.1 mM LLPC aqueous solution (FIG. 12E) and then flushing with pH 8.9, 0.1 M phosphate buffer solution for 15 minutes (FIG. 12F).
Figure 12B:
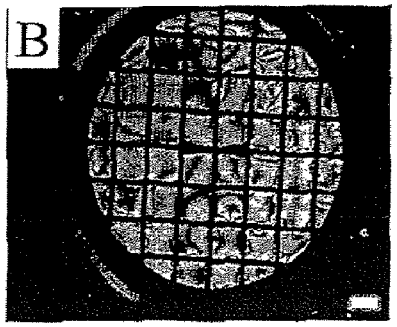
Figure 12C:
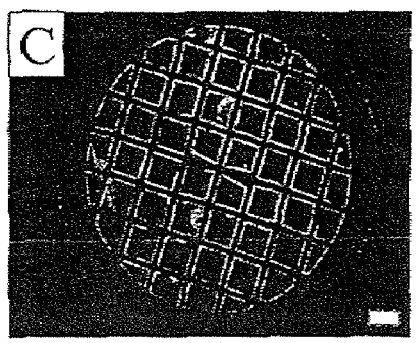
Figure 12D:
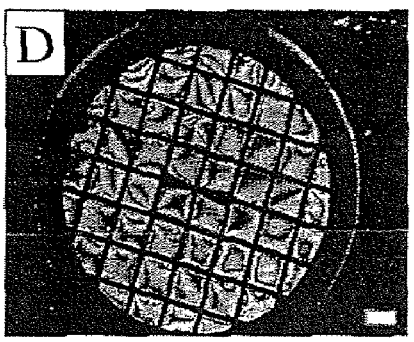
Figure 12E:
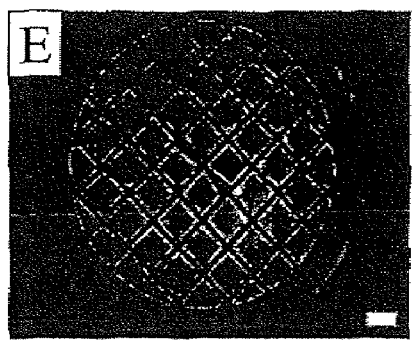
Figure 12F:
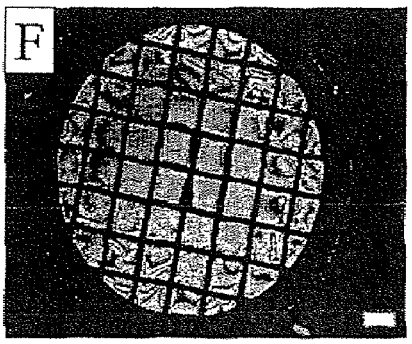

As shown in FIG. 12A, when 5CB confined in a gold grid was contacted for one hour with a 0.1 mM lauric acid aqueous solution, the optical texture appeared bright indicating lack of any substantial interaction between the lauric acid and the 5CB under these conditions. Replacing the lauric acid solution with a 10 mM phosphate, 100 mM sodium chloride aqueous solution at pH 8.9 produced no change in the optical appearance after 15 minutes had elapsed (FIG. 12B). In contrast with the results obtained using lauric acid, when 5CB confined in a gold grid was contacted for one hour with a 0.1 mM LLPC aqueous solution, the optical texture appeared dark (FIG. 12C) indicating formation of an LLPC membrane and a corresponding homeotropic orientation of the liquid crystal. Replacing the LLPC solution with a 10 mM phosphate, 100 mM sodium chloride aqueous solution at pH 8.9 produced a change in the optical appearance from dark (FIG. 12C) to bright (FIG. 12D) after 15 minutes had elapsed. The results with LLPC indicate that it forms a membrane on the surface of the 5CB which is reversibly adsorbed and is removed when the LLPC solution is replaced with an aqueous solution free of LLPC. Results similar to those observed upon contact with LLPC were obtained when the 5CB was exposed to an aqueous solution 0.1 mM in lauric acid and 0.1 mM in LLPC (FIGS. 12E and 12F). The above results indicate that the products of the enzymatic cleavage of DLPC will readily desorb from the liquid crystal at the liquid crystal/aqueous interface giving rise to a change in the orientation of the liquid crystal with adsorbed DLPC upon exposure to $PLA_2$ in the presence of $Ca2^+$ ions.

Example 9

Reversible SDS Adsorption and Membrane Formation on SCB

The effect of the bulk concentration of SOS on the anchoring of 5CB was evaluated at concentrations ranging from 0.01 mM to 100 mM (spanning the critical micelle concentration of SDS at about 8.4 film). Aqueous solutions of SDS having concentrations below 10 mM were prepared by serial dilution of a 10 mM stock solution. The effect of electrolyte concentration on the adsorption of SDS and response of the liquid crystal was further examined by adding sodium chloride to the above SDS solutions in concentrations ranging from 0 to 0.1 M. All SDS solutions were prepared immediately before each experiment to minimize the extent of hydrolysis of SDS during each experiment. SDS solutions were maintained at room temperature, and the liquid crystal cells prepared from copper TEM grids on OTS-treated glass slides were immersed in piranha-cleaned glass dishes (60 mm diameter) containing 20 mL of a given aqueous solution of SOS. Each system was allowed to equilibrate for 5 minutes before optical observations were initiated. The equilibrium alignment of 5CB was observed to occur within 5 minutes of exposure of the 5CB to each aqueous solution of SDS. This observation is consistent with the time-scale for diffusion of SDS to the liquid crystal/aqueous interface for concentrations of 0.1 mM and above <2 minutes). The alignment of 5CB at all SDS concentrations remained unchanged for at least four hours after the initial 5 minute equilibration period when the concentration of SDS was maintained constant. Adsorption of SDS on the top surface of the 5CB resulted in a change in the optical texture from bright to dark indicating a change in the orientation of the 5CB from planar to homeotropic.

The liquid crystal devices formed from the 5CB confined in the copper TEM grids on OTS-treated glass slides were first immersed for at least 5 minutes in a prescribed SDS solution (volume of about 20 mL) to allow the 5CB to obtain its preferred alignment in equilibrium with this solution. The SDS solution was then exchanged with a solution of different concentration of SDS by displacing the solution with at least 100 mL of the new solution (about 5 volumes of the original SDS solution). The 5CB was exposed to the new bulk SDS concentration for 5 minutes to allow re-equilibration of SDS adsorption and realignment of 5CB.

The optical appearance of 5CB confined within copper grids (spacing of 292 µm) on OTS-treated glass slides when contacted with aqueous solutions containing increasing concentrations of SDS was observed and recorded. In the absence of SDS, the optical appearance of 5CB was bright reflecting the in-plane birefringence associated with planar anchoring on the surface of water. For SDS concentrations of up to 0.1 mM, the observed optical texture was similar to that obtained in the absence of SDS, indicating a strong in-plane birefringence at the liquid crystal/aqueous interface and a planar orientation of the 5CB. At SDS concentrations ranging from 0.32 mM to 1 mM, the optical texture of the liquid crystal appeared to be different from that observed at lower concentrations of SDS. At 0.6 mM SDS, the coexistence of homeotropically aligned regions and non-uniformly aligned regions of 5CB was consistently observed. In general, as the SDS concentration increased over this concentration range, the fraction of homeotropically aligned regions of 5CB within the grid increased. The boundaries between these two types of anchoring were generally defined by the grid. This result suggested that the grids compartmentalize the liquid crystal and its interface. Large diffuse brushes that were characteristics of the optical textures of 5CB at low SDS concentrations were absent above SDS concentrations of 0.32 mM. At concentrations of SDS above 1 mM, the optical appearance of 5CB within the grids was uniformly dark, consistent with homeotropic alignment of 5CB. This result was confirmed by conoscopic examination of the sample. Finally, at a bulk SDS concentration of 100 mM, the 5CB alignment was observed to be unstable and highly non-uniform. The appearance of the liquid crystal in these samples changed rapidly over seconds, in contrast to observations using 10 mM SDS or lower, where the orientation was observed to be stable for at least 4 hours. Without being bound by theory, it is hypothesized that the process of solubilization of 5CB into SDS micelles substantially influences the behavior of the system at high SDS concentrations. This proposition was supported by measurements of the absorbance (at 280 nm) of these solutions.

Experiments were performed to determine whether the adsorption of SDS on the top surface of 5CB confined in copper grids on OTS-treated slides was reversible. In these experiments, 5CB confined in the copper TEM grid was sequentially exposed to 10 mM, 0.01 mM, 1 mM, and finally 0.1 mM SDS aqueous solutions. In each case, the optical appearance of the 5CB corresponded to that previously observed for the concentration level of SDS. This confirmed that the orientational behavior of the 5CB was reversible. In an attempt to characterize the dynamics of SDS desorption, another experiment was performed in which the exchange of solution from 10 mM SDS to 0.1 mM SDS was accomplished while observing the optical texture of the cell. The observed realignment of 5CB occurred on a time scale of about 60 seconds which is substantially in excess of the predicted SDS desorption time at an air-water interface. This result likely reflects the effects of mass transport on the system.

It was hypothesized that a change in the orientation could be induced by the addition of a salt such as sodium chloride to SDS solutions. This proposition was confirmed by the results of experiments in which the concentration of SDS was maintained at a constant level while the level of sodium chloride was altered. For example, an aqueous solution containing 0.1 mM SDS and 0.001 M NaCl resulted in an optical appearance of the 5CB within the grid that was consistent with planar anchoring of the 5CB at the liquid crystal/aqueous interface. Addition of 0.1 M NaCl (fixed SDS concentration) induced homeotropic anchoring of 5CB at the aqueous interface indicating greater adsorption by the SDS as the salt concentration increased. At a fixed NaCl concentration of 0.01 M, an orientational transition in the anchoring of 5CB was observed between bulk SDS concentrations of 0.1 mM and 0.32 mM which only occurred at higher concentrations in the absence of the NaCl. Exposure of 5CB to electrolyte (NaCl) dissolved in water with no SDS present resulted in no apparent change in the alignment of 5CB. It was thus concluded that the NaCl, by itself, was not responsible for any change in the orientation of the 5CB.

Example 10

Detection of PLA2 Interaction with Phospholipid Using Substrate with Preformed Wells 5CB is confined to patterned substrates (hole size of 2 μm to 1 cm and thickness of 1 μm to 200 μm) by contacting a 1 μL droplet of 5CB with the patterned region of the surface. Excess 5CB is removed by contacting a 25 μL capillary tube with the 5CB. The resulting film of 5CB confined to the grid is quickly immersed in and withdrawn from deionized water. The 5CB impregnated surface is then immersed in vesicle solutions of phospholipids such as DLPC and DPPC in various buffers such as Tris-buffer. After a layer of the phospholipid is adsorbed between the 5CB and aqueous phase, which is indicated by the transition of the alignment of 5CB to a homeotropic alignment, the aqueous solution is exchanged with a buffer solution that does not contain any lipid. During this exchange, the lipid-laden 5CB interface remains continuously immersed in the aqueous phase. Subsequent exposure to proteins such as $PLA_2$ is accomplished by injecting the protein into the aqueous phase to give the desired total concentration. The optical appearance of the 5CB is monitored using a light microscope with crossed polarizers for polymeric substrates which are optically isotropic and clear. There is no variation in the experimental techniques or optical examination techniques other than the preparation of the patterned substrate and introduction of the 5CB to the surface (see Example 5).

Example 11

Formation of Interfacial Membrane with Phospholipid and Transmembrane Protein

Formation of interfacial layers incorporating proteins is accomplished employing several methods. The preparation of the liquid crystal impregnated grids or patterned substrates as well as the dimensions of the surfaces is the same as in the above Examples. The liquid crystal stabilized by the grid or substrate is immersed in an aqueous buffer of choice such as Tris. The transmembrane protein is then delivered to the liquid crystal-aqueous interface by injecting the protein into the aqueous phase at a desired concentration, for example at 1 μM. After allowing adsorption to progress for a satisfactory time (e.g. 1-2 hours), a vesicle solution of phospholipid (e.g. DLPC) is added to the aqueous phase to give a concentration of 0.1 DIM. The adsorption is then allowed to continue until equilibrated (e.g. 30-120 minutes). Equilibration is identified by a uniform alignment of the liquid crystal (such as homeotropic alignment). In some examples. introduction of the protein occurs along with introduction of the lipid. In other examples, the lipid is first adsorbed and then the protein is added. After both the protein and the lipid have been deposited on the liquid crystal, the aqueous solution is exchanged for an appropriate buffer which does not contain the protein or the lipid. Further addition of analytes to the aqueous phase is initiated at this point.

Example 12

Use of Liquid Crystals to Detect Structural Changes in the Adsorbed Surfactant Layer 5CB was confined to copper TEM grids (hole size 29 μm, thickness 18-20 μm) placed on OTS-treated glass slides by contacting a 1 mL droplet of 5CB with the grid. Excess 5CB was removed by contacting a 25 μL capillary tube with the 5CB. The resulting film of 5CB confined to the grid was quickly immersed in and withdrawn from deionized water. The 5CB impregnated grid on the OTS-treated glass slide was then immersed in the indicated surfactant solution. The system was allowed to equilibrate until no further change in the optical texture of the 5CB was observed, typically 15 minutes. The optical appearance of the 5CB was monitored using a light microscope with crossed polarizers and all images shown were taken at a magnification of 4× with an incident light aperture of 10% and a relative light source intensity of 50%.

Figure 13A:
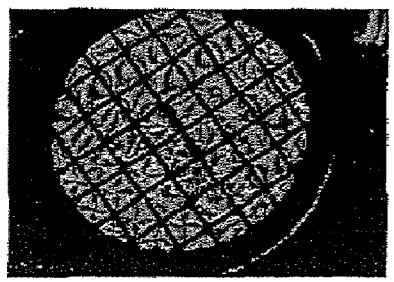
FIGS. 13A-13F are scanned images through an optical microscope with cross-polarizers of the optical texture of 5CB confined to a copper grid after exposure to a 0.01 mM DBTAB aqueous solution (FIG. 13A); after exposure to a 100 mM DTMAD aqueous solution (FIG. 13B); after exposure to a 0.01 mM HTAB aqueous solution (FIG. 13C); after exposure to a 10 mM HTAB aqueous solution (FIG. 13D); after exposure to a 1 µM CTAB aqueous solution (FIG. 13E); and after exposure to a 10 µM CTAB aqueous solution (FIG. 13F).
Figure 13B:
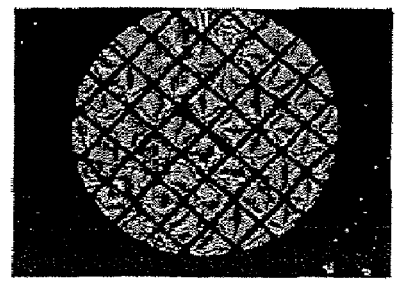
Figure 13C:
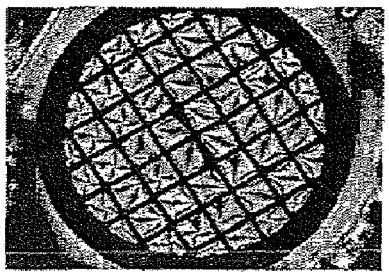
Figure 13D:
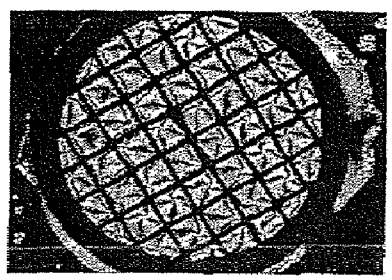
Figure 13E:
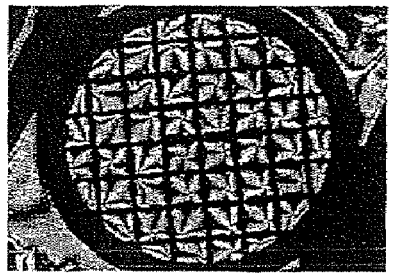
Figure 13F:
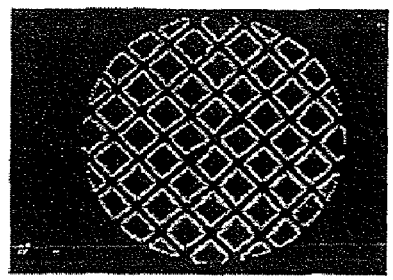

FIGS. 13A-13F are images through an optical microscope with cross-polarizers of the optical texture of 5CB confined to a copper grid after exposure to an aqueous solution containing 0.01 mM DBTAB (FIG. 13A); after exposure to an aqueous solution containing 100 mM DBTAB (FIG. 13B); after exposure to an aqueous solution containing 0.0 mM HTAB (FIG. 13C); after exposure to an aqueous solution containing 10 mM HT AB (FIG. 13D); after exposure to an aqueous solution containing 1 μM CTAB (FIG. 13E); and after exposure to an aqueous solution containing 10 μM CTAB (FIG. 13F). All aqueous surfactant solutions contained 0.1 M $Li_2SO_4$ and were at a pH of 2.

As shown in FIGS. 13A-13D, the alignment of the 5CB is planar upon contact with the various surfactant solutions. This result indicates that the alignment of the 5CB remains indiscriminant of the amount of adsorbed surfactant within the concentration ranges examined. In contrast, FIGS. 13E and 13F show that the 5CB undergoes an alignment change due to increasing bulk concentration and, presumably, interfacial concentration of CT AB. The difference in the response of the 5CB is believed to be due to the nature of the adsorbate. DBT AB and HT AB both have hydrophilic components on each end of an aliphatic chain. Thermodynamically, these molecules will prefer to adsorb at oil interfaces with both hydrophilic headgroups in contact with the aqueous phase while the aliphatic chain remains in the liquid crystal phase resulting in a looped, or bolaform, orientation of the surfactant at the interface. CT AB, however, has only one hydrophilic headgroup allowing the molecule to adsorb with the aliphatic chain slightly tilted or perpendicular relative to the interface between the 5CB and water. Therefore, the results indicate that the orientation of the aliphatic chain can dictate the orientation of the liquid crystal allowing this invention to detect changes in the molecular structure of the 5CB-water interface.

Example 13

Use of Liquid Crystals to Detect Changes in the Oxidation State of Adsorbed Surfactant Layers The liquid crystal 5CB was confined to copper TEM grids (hole size 292 μm, thickness 18-20 μm) placed on OTS-treated glass slides by contacting a 1 mL droplet of 5CB with the grid. Excess 5CB was removed by contacting a 25 μL capillary tube with the 5CB. The resulting film of 5CB confined to the grid was quickly immersed in and withdrawn from deionized water. The 5CB impregnated grid on the OTS-treated glass slide was then immersed in the indicated surfactant solution in 0.1 M $Li_2SO_4$ at pH 2 for the time indicated. Electrochemical oxidation and reduction of FTMA were performed by connecting the surfactant solution containing the 5CB impregnated grids to a solution of just the buffer via a salt bridge. A working electrode and a reference electrode were placed in the dish containing the surfactant and 5CB impregnated grids. A counter electrode was placed in the dish containing the buffer. The indicated potentials were controlled and the current monitored using a potentiostat. The dishes were made of glass allowing the entire apparatus to be placed on the optical stage of a microscope for continuous observation of the anchoring of 5CB within the grids. The optical appearance of the 5CB was monitored using a light microscope with crossed polarizers and all images shown were taken at a magnification of 4× with an incident light aperture of 10% and a relative light source intensity of 50%.

Figure 14A:
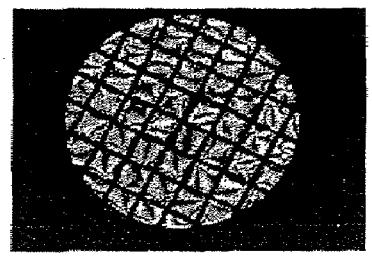
FIGS. 14A-14H are scanned images through an optical microscope with cross-polarizers of the optical texture of 5CB confined to a copper grid after exposure to a 1 mM reduced FTMA 0.1 M Li$_2$SO$_4$ aqueous solution at pH 2 for 5 minutes (FIG. 14A); after exposure to a 1 mM oxidized FTMA 0.1 M Li$_2$SO$_4$ aqueous solution at pH 2 for 5 minutes (FIG. 14B); after exposure to a 5 µM CTAB and 50 µM reduced FTMA 0.1 M Li$_2$SO$_4$ aqueous solution at pH 2 for 90 minutes (FIG. 14C); after exposure to a 5 µM CTAB, 50 µM oxidized FTMA, and 0.1 M Li$_2$SO$_4$ aqueous solution at pH 2 for 5 minutes (FIG. 14D); after exposure to a 5 µM CTAB, 50 µM FTMA, and 0.1 M Li$_2$SO$_4$ aqueous solution at pH 2 with an applied reducing potential of −0.2 V after 120 minutes (FIG. 14E) and then after an applied oxidizing potential of +0.35 V for 210 minutes (FIG. 14F); and after exposure to a 5 µM CTAB, 35 µM FTMA 0.1 M Li$_2$SO$_4$ aqueous solution at pH 2 with an applied oxidizing potential of +0.35 V after 120 minutes (FIG. 14G) and then after an applied reducing potential of −0.20 V for 180 minutes (FIG. 14H).
Figure 14B:
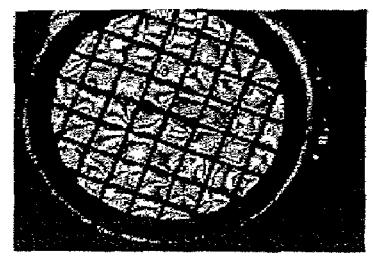
Figure 14C:
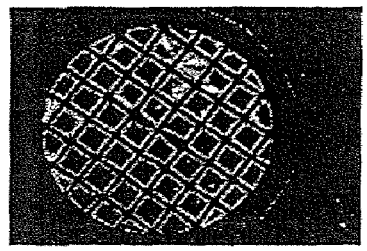
Figure 14D:
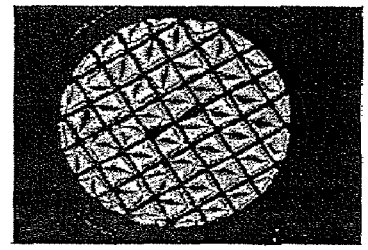
Figure 14E:
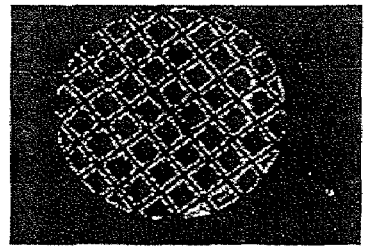
Figure 14F:
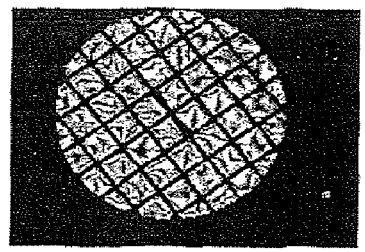
Figure 14G:
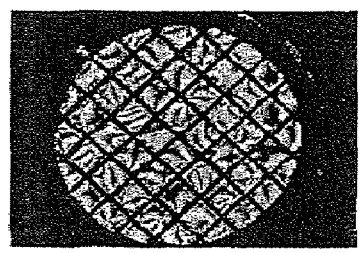
Figure 14H:
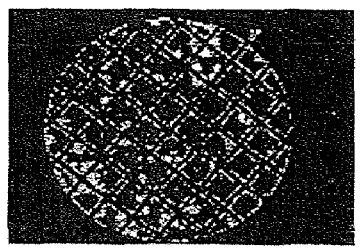

FIGS. 14A-14H are scanned images obtained through an optical microscope with cross-polarizers of the optical texture of 5CB confined to a copper grid after exposure to an aqueous solution containing 1 mM reduced FTMA (11-(ferrocenylundecyl)trimethylammonium bromide) for 5 minutes (FIG. 14A); after exposure to a 1 mM oxidized FTMA aqueous solution for 5 minutes (FIG. 14B); after exposure to an aqueous solution containing 5 μM CTAB and 50 μM reduced FTMA for 90 minutes (FIG. 14C); after exposure to an aqueous solution containing 5 μM CTAB and 50 μM oxidized FTMA for 5 minutes (FIG. 14D); after exposure to an aqueous solution containing 5 μM CTAB and 50 μM FTMA with an applied reducing potential of −0.2 V for 120 minutes (FIG. 14E) and then an applied oxidizing potential of +0.35 V for 210 minutes (FIG. 14F); and after exposure to an aqueous solution containing 5 μM CTAB and 50 μM FTMA with an applied oxidizing potential of +0.35 V for 120 minutes (FIG. 14G) and then an applied reducing potential of −0.2 V for 180 minutes (FIG. 14H). All surfactant solutions contained 0.1 M $Li_2SO_4$ and were at a pH of 2.

FIGS. 14A and 14B show that the anchoring of 5CB is insensitive to the oxidation state of the FTMA in the absence of CTAB. FIGS. 14C and 14D show that, by adding CTAB at an appropriate concentration to the FTMA solutions, the 5CB becomes sensitive to the oxidation state of the FTMA. This result demonstrates that, by using mixtures of surfactants, interfaces may be created which are close to an anchoring transition of the 5CB allowing for increased sensitivity in detection schemes. FIGS. 14E-14H show that it is possible to reversibly switch the alignment of the 5CB by controlling the oxidation state of a surfactant such as FTMA using electrochemistry. This result demonstrates that this experimental system can be applied to display applications using low voltages (about 0.2-0.35 V) to trigger alignment changes in the liquid crystal. These results also demonstrate the sensitivity of the alignment of 5CB within the experimental system to changes in the electrostatic nature of the liquid crystal-aqueous interface.

Example 14

Formation of Liquid Crystal Device Using Surfactant Dissolved in a Liquid Crystal DPPC is dissolved in a solvent such as hexane, chloroform, or methylene chloride. 500 μL of this organic solution is then added to 100 μL of 5CB, and the solvent is evaporated producing a mixture containing DPPC and the liquid crystal. Concentrations of phospholipid in the liquid crystal are chosen to provide at least enough moles to obtain a desirable surface concentration, typically 0.2-10 $nm_2$/molecule. In a second example, the DPPC is dissolved or dispersed directly in the liquid crystal without the use of an organic solvent such as hexane, chloroform, or methylene chloride. The DPPC/5CB mixture is then deposited in the depressions of grids of a substrate according to any of the methods described herein. The top surface of the liquid crystal/phospholipid mixture in the grids or depressions is then exposed to an aqueous solution by immersing the substrate in the aqueous solutions. In another example, the aqueous solution flows over the surface of the liquid crystal/phospholipid mixture. Either method is acceptable provided that the surface of the liquid crystal remains in continuous contact with the aqueous phase. The adsorption of the DPPC at the 5CB-aqueous interface occurs spontaneously and is monitored by observing the optical texture of the liquid crystal using a polarized light microscope. The optical appearance of the 5CB indicates homeotropic orientation at the 5CB-aqueous interface.

Example 15

Formation of Liquid Crystal Device with Multiple Receptors in Different Holding Compartments 5CB was confined to copper TEM grids (hole size 292 μm, thickness 18-μm) placed on OTS-treated glass slides by contacting a 1 μL droplet of 5CB with the grid. Excess 5CB was removed by contacting a 25 μL capillary tube with the 5CB. Two grids were hosted on a single OTS-coated glass slide which were impregnated with 5CB. A 10 μL droplet of 0.1 mM DLPC in Tris buffer was placed over one of the 5CB impregnated grids while a 10 μL droplet of 0.1 mM DPPC in Tris buffer was placed over the second 5CB impregnated grid. The system was allowed to equilibrate until no further change in the optical texture of the 5CB was observed, typically 2 hours. The surface was held at the dew point to prevent evaporation of the droplet during the adsorption process. After the adsorption was complete, the slide was placed in a solution containing only Tris buffer (volume of about 20 mL). The optical appearance of the 5CB was monitored using a light microscope with crossed polarizers. Homeotropic alignment of the 5CB was observed within each grid indicating that the deposition of the two lipids occurred.

Example 16

Specific Binding of Biotin Receptor Molecules to a Biotinylated Lipid Layer Imaged Using Liquid Crystals 5CB was confined to gold TEM grids (hole size of 292 μm and, thickness of 18-20 μm) placed on OTS-treated glass slides by contacting a 1 μL droplet of 5CB with the grid. Excess 5CB was removed by contacting a 25 μL capillary tube with the 5CB. The 5CB impregnated grid on the OTS-treated glass slide was then immersed in vesicle solutions of 70% DPPC, 30% biotin-conjugated DPPE (Molecular Probes, Eugene, Oreg.) (0.1 mM total concentration) in PBS, After sufficient adsorption of the phospholipid was observed by homeotropic orientation of the contacting 5CB (typically 2 hours), the vesicle-containing PBS solution was exchanged with a PBS solution free of phospholipids. The system was allowed to equilibrate for 15 minutes before injecting various protein solutions. The optical appearance of the 5CB was monitored using a light microscope with crossed polarizers.

The specific proteins used in this study were NeutrAvidin (Pierce, Rockford, Ill.) and BSA. When the mixed DPPC/biotinylated DPPE layers were exposed to NeutrAvidin at a concentration of 100 nM, the texture of the liquid crystal was observed to change irreversibly over the course of 21 hours. The appearance of the liquid crystals became completely bright when viewed between crossed polars. In contrast, when the DPPC/biotinylated DPPE layers were exposed to 100 nM NeutrAvidin that is blocked by the injection of an excess concentration of free biotin into the solution, the resulting 5CB texture after 21 hours had an appearance that was distinct from that observed without blocking of the NeutrAvidin with free biotin. Specifically, the appearance of the liquid crystals is less bright and large regions of homeotropic alignment (black appearance between crossed polars) were observed in the blocked sample. This result demonstrates that the appearance of the liquid crystal is dependent on the extent of binding of NeutrAvidin to the biotinylated DPPE.

Exposure of the DPPC/biotinylated DPPE layers to BSA also resulted in an irreversible change in 5CB texture over the course of 21 hours. However, the texture observed when the lipid layer was exposed to BSA was distinguishable from the texture observed when the lipid layer was exposed to NeutrAvidin. In the case of BSA, the domains which formed in the 5CB had schlieren textures not observed when NeutrAvidin was present. This difference in texture demonstrates that the texture of the 5CB is sensitive to the nature of the interaction of the two proteins with the lipid layer allowing for discrimination of binding and non-specific interactions.

It is understood that the invention is not limited to the embodiments set forth herein for illustration, but embraces all such forms thereof as come within the scope of the claims.

What is claimed is:

1. A method of forming a liquid crystal device, comprising:
    contacting an aqueous solution with a top surface of a liquid crystal solution comprising a liquid crystal and a surface-active compound dispersed or dissolved therein, wherein the liquid crystal solution is located in a holding compartment of a substrate, and further wherein the surface-active compound migrates to the top surface of the liquid crystal solution upon contact with the aqueous solution forming an interfacial layer between the liquid crystal and the aqueous solution.

2. The method of claim 1, wherein the liquid crystal is 4-cyano-4'-pentylbiphenyl.

3. The method of claim 1, wherein the surface-active compound is a phospholipid.

4. The method of claim 1, wherein the substrate comprises a grid disposed on a hydrophobic surface of glass support and the grid defines a cavity comprising the holding compartment of the substrate.

5. The method of claim 1, wherein the substrate comprises a support with a top surface that defines at least one depression which comprises the holding compartment of the substrate.

* * * * *